United States Patent
Klaerner et al.

(10) Patent No.: US 6,472,486 B2
(45) Date of Patent: *Oct. 29, 2002

(54) CONTROLLED STABLE FREE RADICAL EMULSION POLYMERIZATION PROCESSES

(75) Inventors: Gerrit Klaerner, Campbell; Adam Safir, Oakland; Ralph B. Nielsen, San Jose; Bernd Jandeleit, Palo Alto; Peter Huefner, San Jose, all of CA (US)

(73) Assignee: Symyx Technologies, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/347,609

(22) Filed: Jul. 2, 1999

(65) Prior Publication Data

US 2002/0061988 A1 May 23, 2002

Related U.S. Application Data

(60) Provisional application No. 60/123,498, filed on Mar. 9, 1999.

(51) Int. Cl.[7] .................. C08F 2/22; C08F 2/38
(52) U.S. Cl. .............. 526/220; 526/193; 526/201; 526/217; 526/227; 526/922
(58) Field of Search .................. 526/193, 201, 526/211, 217, 220, 227, 236, 922

(56) References Cited

U.S. PATENT DOCUMENTS

| | | | |
|---|---|---|---|
| 3,422,144 A | * 1/1969 | Hoffmann et al. | 260/570 |
| 3,985,830 A | 10/1976 | Fetters et al. | |
| 4,093,586 A | 6/1978 | Stephen | 260/45.8 |
| 4,581,429 A | 4/1986 | Solomon et al. | 526/220 |
| 4,783,508 A | 11/1988 | Moore et al. | 525/310 |
| 4,792,593 A | 12/1988 | Schulz et al. | 526/240 |
| 5,270,271 A | 12/1993 | Ludin et al. | 502/8 |
| 5,322,912 A | * 6/1994 | Georges et al. | 526/204 |
| 5,346,545 A | 9/1994 | Chassot | 106/410 |
| 5,374,729 A | 12/1994 | Galbo | 546/242 |
| 5,385,996 A | 1/1995 | Rizzardo et al. | 526/240 |
| 5,389,141 A | 2/1995 | Chassot | 106/498 |
| 5,401,804 A | 3/1995 | Georges et al. | 525/267 |
| 5,504,243 A | 4/1996 | Sakamoto et al. | 560/205 |
| 5,582,960 A | 12/1996 | Nielsen et al. | 430/508 |
| 5,652,289 A | 7/1997 | Eisenhart et al. | 524/376 |
| 5,698,648 A | 12/1997 | Rizzardo et al. | 526/232 |
| 5,711,767 A | 1/1998 | Gande et al. | 44/423 |
| 5,714,993 A | 2/1998 | Koeshkerian | |
| 5,723,511 A | 3/1998 | Kazmaier et al. | |
| 5,728,747 A | 3/1998 | Kazmaier et al. | 522/11 |
| 5,760,124 A | 6/1998 | Listigovers | |
| 5,804,619 A | 9/1998 | Nicol et al. | 524/68 |
| 5,830,966 A | 11/1998 | Thang et al. | 526/321 |
| 5,844,025 A | 12/1998 | Cunkle et al. | 524/99 |
| 5,874,511 A | 2/1999 | Rizzardo et al. | 526/286 |
| 5,877,344 A | 3/1999 | Gande et al. | 560/205 |
| 5,919,871 A | 7/1999 | Nicol et al. | 525/333 |
| 6,121,397 A | * 9/2000 | MacLeod et al. | 526/204 |
| 6,255,448 B1 | 7/2001 | Grimaldi et al. | 528/398 |

FOREIGN PATENT DOCUMENTS

| | | | |
|---|---|---|---|
| EP | 0 135 280 A2 | 3/1985 | |
| EP | 0887362 A1 | 12/1996 | |
| EP | 891 986 | * 1/1999 | C08F/2/00 |
| EP | 0891 986 A1 | 1/1999 | |
| EP | 0891 997 A1 | 1/1999 | |
| EP | 0970973 | 12/2000 | |
| GB | 1 218 456 | 1/1971 | |
| WO | WO 96/18609 | 6/1996 | C07C/303/24 |
| WO | WO-96/24620 A1 | * 8/1996 | C08F/4/00 |
| WO | WO 96/24620 | 8/1996 | |
| WO | WO 96/30421 | 10/1996 | |
| WO | WO 97/36944 | 10/1997 | |
| WO | WO 97/46593 | 12/1997 | |
| WO | WO 98/01478 | 1/1998 | |
| WO | WO 98/01480 | 1/1998 | |
| WO | WO 98/07758 | 2/1998 | |
| WO | WO 98/13392 | 4/1998 | |
| WO | WO 98/20050 | 5/1998 | |
| WO | WO 98/30601 | 7/1998 | |
| WO | WO 98/58974 | 12/1998 | |
| WO | WO 99/00426 | 1/1999 | |
| WO | WO 99/00427 | 1/1999 | |
| WO | WO 99/03894 | * 1/1999 | C08F/2/00 |
| WO | WO 99/46261 | 9/1999 | C07D/405/12 |

OTHER PUBLICATIONS

Grimaldi et al. [Synthesis and Application of "Living" Free Radical Polymerization of a New Class of Nitroxyl Radicals, Polymers Preprints, 38 (1), pp. 651–652 (1997)].*

Benoit et al. [Controlling Free-Radical polymerization in the Presence of a Novel Asymmetric Nitroxyl Radical), Polymer Preprints, 38 (1), pp. 729–730 (1997)].*

C. Marestin, et al., "Nitroxide Mediated Living Radical Polymerization of Styrene in Emulsion," *Macromolecules* 31(12):4041–4044; Jun. 16, 1998.

M. Lansalot et al., "Nitroxide-Mediated Controlled Free-Radical Emulsion Polymerization of Styrene," *Am. Chem. Soc.* 'Polymer Preprints,' 40(2):317–318; 1999; New Orleans, LA, USA.

(List continued on next page.)

*Primary Examiner*—David W. Wu
*Assistant Examiner*—Kelechi Egwim
(74) *Attorney, Agent, or Firm*—Fish & Richardson P.C.

(57) ABSTRACT

Controlled stable free radical emulsion polymerization processes employ nitroxide control agents having an alpha carbon atom bearing a destabilizing substituent such as hydrogen. The emulsion polymerizations have living characteristics, including the re-initiation of polymer chains, and provide a high degree of control over molecular weight, particle size, polydispersity and polymer composition and architecture. The processes are useful for the preparation of polymer emulsions, including block copolymers, star and graft copolymers, telechelics and macromonomers from a wide range of monomers.

60 Claims, 12 Drawing Sheets

OTHER PUBLICATIONS

Benoit et al., "Development of a Universal Alkoxyamine for "Living" Free Radical Polymerizations", J. Am. Chem. Soc., 1999, 121, 3904–3920.

Grimaldi et al., "Synthesis and Applications to "Living" Radical Polymerization of a New Class of Nitroxyl Radicals" Polymer Preprints, vol. 38, No. 1, Apr. 1997, 651–654.

Janzen et al., "Detection and Identification of Short–Lived Free Radicals by Electron Spin Resonance Trapping Techniques", J. Am. Chem. Soc., 1969, 4481–4490.

Janzen et al., "ENDOR Spectra of Aminoxyls. Conformational Study of Alkyl and Aryl Spin Adducts of Deuterated a–Phenyl–N–tert–butylnitrone Based on Proton and . . . ", J. Am. Chem. Soc., 1986, 108, 6858–6863.

Kotake et al., "Bimodal Inclusion of Nitroxide Radicals by b–cyclodextrin in Water as Studied by Electron Spin Resonance and Electron Nuclear Double Resosance", J. Am. Chem. Soc. 1989, 111, 2066–2070.

Malmstrom et al., "Development of a New Class of Rate–Accelerating Additives for Nitroxide–Mediated "Living" Free Radical Polymerization", Tetrahedron, 1997, 15225–15236.

Prodpran et al., "Nitroxide–Mediated Living Free Radical Miniemulsion Polymerization of Styrene", Presented at 217th National Meeting, Amer. Chem. Soc., Anaheim, CA March 24, 1999, 534–535.

Wang et al., "Characterization of Water–Soluble Oligomer in Acrylic Acid–Styrene Emulsion Copolymerization", J. of Applied Polymer Sci., 1993, 30, 2173–2183.

Ucelstad et al., "A Kinetic Investigation of the Emulsion Polymerzation of Vinyl Chloride", J. Polymer Sci. Part C., 1969, 49–68.

Bon et al., "Controlled–Radical Polymerization in Emulsion", Macromolecules, vol. 30, No. 2, pp. 324–326 (1997).

Carvalho et al., "Morphology of Steps in Terraced Block Copolymer Films", Phs. Rev. Ltrs., vol. 73, No. 24, pp. 3321–3324 (1994).

Coulon et al., "Interference microscopy on thin diblock copolymer films", J. Phys. France, vol. 51, pp. 777–786 (1990).

Dao et al., "A Versatile and Efficient Synthesis of Alkoxyamine LFR Initiators via Manganese Based Asymmetric Epoxidation Catalysts", J. Polym. Sci. Part A: Polym. Chem., vol. 36, pp. 2161–2167 (1998).

Dondoni et al., "Synthesis of N–Benzyl Nitrones", Synthetic Comm., vol. 24, No. 18, pp. 2537–2550 (1994).

Georges et al., "The Stable Free–Radical Polymerization Process: Role of Excess Nitroxide", Amer. Chem. Soc., ACS Symposium Series, No. 685, 213th National Mtg., Chapter 10, pp. 170–179 (1998).

Fitch et al., "Emulsion polymerization: Kinetics of radical capture by the particles", Progress in Colloid and Polymer Science, vol. 56, pp. 1–11 (1975).

Kotake et al., "Bimodal Inclusion of Nitroxide Radicals by β–Cyclodextrin in Water As Studied by Electron Spin Resonance and Electron Nuclear Double Resonance", J. Am. Chem. Soc., vol. 111, No. 6, pp. 2066–2070 (1989).

Marestin et al., "Direct Measurement of Oligomers Entry Rate onto Latex Particles in a Emulsion Polymerization", Macromolecules, vol. 31, No. 5, pp. 1686–1689 (1998).

Maxwell, et al., "Entry of Free Radicals into Latex Particles in Emulsion Polymerization", Macromolecules, vol. 24, No. 7, pp. 1629–1640 (1991).

Roberts et al., "Neopentyl Ester Protecting Groups for Arylsufonic Acids", Tetrahedron Letters, vol. 38, No. 3, pp. 355–358 (1997).

Russell et al., "Characteristics of the Surface–Induced Orientation for Symmetric Diblock PS/PMMA Copolymers", Macromolecules, vol. 22, No. 12, pp. 4600–4606 (1989).

Wang et al., "Characterization of Water–Soluble Oligomer in Acrylic Acid–Styrene Emulsion Copolymerization", J. Applied Polymer Science, vol. 50, pp. 2173–2183 (1993).

\* cited by examiner

CONTROLLED STABLE FREE RADICAL EMULSION POLYMERIZATION PROCESSES

CROSS REFERENCE TO RELATED APPLICATIONS

This application claims priority under 35 U.S.C. §119 to the commonly owned, co-pending U.S. Provisional Application No. 60/123,498, filed Mar. 9, 1999, which is incorporated herein by reference in its entirety.

BACKGROUND OF THE INVENTION

1. Field of the Invention

This invention pertains to methods and compositions for controlled free radical polymerization in heterogeneous aqueous media using stable free radicals that provide control under a variety of conditions and with a wide variety of monomers. This invention also pertains to the polymers, copolymers and interpolymers that can be made with such systems. Further, this invention pertains to new methods of initiating such polymerization reactions.

2. Discussion

Controlled free radical polymerizations are generally known that allow "living type" polymerization to occur. These reactions typically proceed by either an atom transfer or stable radical mechanism. Other mechanisms are known, including "iniferter" mechanism and degenerative radical transfer mechanism. In connection with the stable radical mechanism, typically, a stable free radical is used to reversibly cap the propagating polymer chain, and there are several well-known nitroxides that may be usefully employed. See, e.g., U.S. Pat. Nos. 4,581,429, 5,322,912 and 5,401,804, each of which is incorporated herein by reference. The nitroxides disclosed. in these references have carbon atoms attached to the nitrogen (i.e., α-carbon atoms) that bear alkyl or aryl moieties. One of the most common nitroxide radicals is 2,2,6,6-tetramethyl-1-piperidinoxyl radical (TEMPO) and several groups have worked to make this and related radicals a commercially viable control agent in a stable free radical polymerization scheme. See, e.g., WO 98/13392 and WO 98/07758. The drawback of using TEMPO and related stable radicals has been the limitation on the monomers that can actually be polymerized, the high temperatures required, and an inability to function well in emulsions. Styrene, substituted styrenes and copolymers including styrene have been prepared, but other desirable, commercially important monomers have not been polymerized successfully in a controlled manner to desired molecular weights. TEMPO has proven to be limited in its usefulness, while others have suggested that structures similar to TEMPO have greater usefulness. See WO 98/30601, which is incorporated herein by reference.

Alternative nitroxides were suggested by Grimaldi et al. bearing an electron withdrawing dialkoxyphosphonyl substituent and a hydrogen atom on the carbon atoms in the α-position relative to the nitrogen. Grimaldi et al. "Synthesis and Applications to 'Living' Free Radical Polymerization of a New Class of Nitroxyl Radicals," Polymer Preprints, vol. 38, no. 1 (April 1997). See also WO 96/24620. By comparing the α-substituted dialkoxyphosphonyl nitroxides to other nitroxides having alkyl substituents and a hydrogen atom on an α-carbon, Grimaldi et al. concluded that the dialkoxyphosphonyl nitroxides provide better control and access to a greater range of monomers than TEMPO. See also EP 0891 986 A1, which is incorporated herein by reference.

Recently, Hawker et al. have shown that it is the presence of a hydrogen atom on the α-carbon, rather than the dialkoxyphosphonyl group that provides a route to the controlled free radical polymerization of monomers other than styrene. Hawker et al. "Development of a Universal Alkoxyamine for 'Living' Free Radical Polymerizations," *J. Am. Chem. Soc.*, 1999, 121, 3904–3920. Also, it should be noted that many stable nitroxide radicals having a hydrogen atom on the α-carbon (sometimes referred to as α-hydrido nitroxides) are known. See, e.g., Janzen et al., *J. Am. Chem. Soc.*, 1969, 91,4481–4490; Janzen et al., *J. Am. Chem. Soc.*, 1989, 111, 2206–2070; and Janzen et al., *J. Am. Chem. Soc.*, 1986, 108, 6858–6863.

These efforts have typically focused on polymerizations in bulk and in organic solution. However, the use of water as a dispersing medium for control free radical polymerization is commercially important for several reasons. First, water is a safe medium from an environmental viewpoint, facilitating the manufacture of consumer products (such as paints or glues). Also, water is inexpensive, providing an economical process. Moreover, the various emulsion polymerization processes can offer mechanistic and process advantages over homogeneous polymerization, in terms of reaction kinetics, molecular weight, viscosity, heat transfer, and resulting polymer structures and properties. Also, many applications of polymers directly utilize the heterogeneous aqueous polymer products of such polymerization.

Known uncontrolled or non-living aqueous heterogeneous polymerization processes are useful because they can produce a wide variety of polymer products utilizing many types of monomers in rapid economical processes at temperature below 100° C., forming polymer particles with controlled particle sizes and polymers of high molecular weight. However, such non-living processes allow limited or no control over the polymer chain architecture, such as the formation of block copolymers or formation of narrow molecular weight distribution.

The known living or controlled polymerization processes can offer controlled chain architecture and molecular weight distribution. However, such processes have typically required very high temperatures,>100° C., utilize only limited types of monomers, produce polymer in slow, time-consuming process, and do not work well in heterogeneous aqueous media. The few heterogeneous aqueous system known require high temperature or produce polymer particles. with limited control of particle size and distribution.

Thus, a need exists for a versatile, heterogeneous water-based controlled or living free radical polymerization process, which can polymerize many different types of monomers with economically viable process conditions.

SUMMARY OF THE INVENTION

This invention is thus directed toward methods of polymerization to form heterogeneous aqueous polymer mixtures such as emulsions. The methods of this invention provide stable, living-type free radical polymerizations in an emulsion, including the ability to re-initiate polymer chains and thus prepare unique polymers and architectures, such as block copolymers, including stars, grafts, telechelics and macromonomers. It is also an object of this invention to provide a polymerization process that allows access to a wide variety of monomers that may be polymerized alone or together in emulsions. Moreover, some methods of this invention enable access to a full range of initiators, including fast and water-soluble initiators as well as slow and organic-soluble initiators that might otherwise appear to be less favorable for aqueous-based living polymerizations. It is also an object of this invention to enable the preparation of polymer emulsions with excellent control over particle size, molecular weight, polydispersity and polymer composition and architecture.

These and other benefits can be realized by an emulsion polymerization process that uses water, initiator, at least one monomer and a control agent that is an α-hydrido nitroxide. The control agent can be added to the emulsion as a stable free radical, as an adduct with the initiator or as a nitrone precursor. The ratio of control agent to initiator can be in the range of from about 0.01:1 to about 4:1, but is preferably close to 1:1 to provide a commercially reasonable balance between reaction time and living character. The ratio of initiator to monomer is important to the desired molecular weight of the resultant polymer and this ratio can be adjusted to a desired target molecular weight.

Yet another aspect of this invention is a novel process for an emulsion polymerization that allows the use of slow initiators or organic soluble initiators for a living-type emulsion polymerization mixture. This novel process overcomes these problems in an emulsion system by supplying the monomer to the process in two or more stages. First, a fraction of the total monomer that is planned to be added to the polymerization reaction is first mixed with the initiator, control agent, water and surfactant. This combination is mixed and allowed to react for a predetermined period of time under predetermined polymerization conditions. The intent of this first stage is to allow nearly complete reaction of the initiator to form "living" oligomers with the monomer in the system and the control agent. Second and optionally subsequent stages provide for the addition of additional monomer, which can be the same or different from the monomer used in the first stage.

DETAILED DESCRIPTION

Figure 1A:
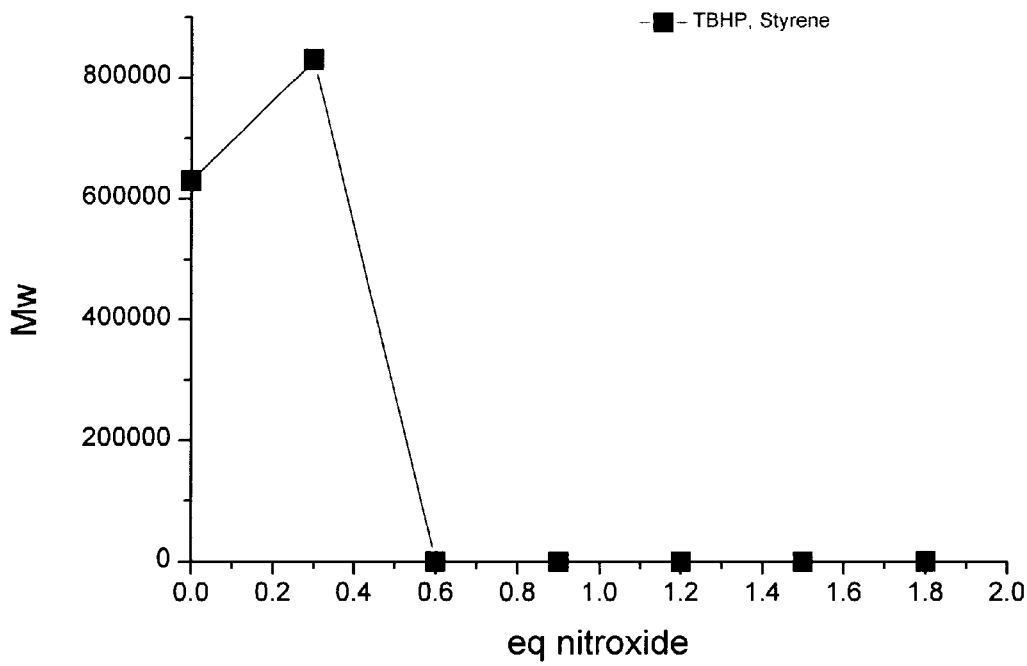
FIGS. 1A and 1B are graphs showing molecular weight and conversion as a function of increasing nitroxide concentration for the TEMPO-controlled heterogeneous polymerization of styrene.

The present invention is directed toward a polymerization process that uses a nitroxide control agent in heterogenous aqueous conditions and polymers made by that process. The control agent provides living type kinetics to the polymerization system. This invention also is directed toward a method of heterogeneous aqueous free radical polymerization that allows otherwise slow initiators or organic soluble initiators to be used in a heterogeneous aqueous living type free radical polymerization process.

As used herein, the phrase "characterized by the formula" is not intended to be limiting and is used in the same way that "comprising" is commonly used. The term "independently selected" is used herein to indicate that the R groups, e.g., $R^1$, $R^2$ and $R^3$ can be identical or different (e.g. $R^1$, $R^2$ and $R^3$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, isopropyl, propenyl (or allyl), hexyl, vinyl, n-butyl, tert-butyl, iso-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Se and Ge. The bond between the carbon atom and the heteroatom may; be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl, $Me_3SiOCH_2(CH_3)_2C$— and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorus, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl, and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholine, and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Specific example of substituted aryls include perfluorophenyl, chlorophenyl, 3,5-dimethylphenyl, 2,6-diisopropylphenyl and the like.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the $-OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy; etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the $-SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the $-BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group $-PZ^n$, where each of $Z^n$ is independently selected from the group consisting of hydrogen oxygen, substituted or unsubstituted alkyl, cycloalkyl, heterocycloalkyl, heterocyclic, aryl, heteroaryl, silyl, alkoxy, aryloxy, amino and combinations thereof, where n is z to 4 depending on the phosphorus oxidation state.

The term "amino" is used herein to refer to the group $-NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group $-SZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group $-SeZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like.

The free radical control agents that are useful in this invention may be characterized by the general formula:

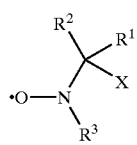

(I)

where each of $R^1$, $R^2$ and $R^3$ are the same or different straight chain, branched or cyclic substituted or unsubstituted alkyl groups, including, for example, hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; $R^1$ and $R^2$ may be joined together in a cyclic ring structure; likewise, $R^2$ and $R^3$ may be joined together in a cyclic ring structure that may have fused with it another saturated or aromatic ring; and X is a moiety that is capable of destabilizing the free radical. By "capable of destabilizing" it is meant that the X moiety allows the free radical to destabilize, decompose, be destroyed, or otherwise removed from the reaction, or be destabilized, decomposed, destroyed or removed from the reaction by the addition of a reagent. For the aqueous applications of this invention, it is frequently preferred that one of the R groups ($R^1$, $R^2$ or $R^3$) includes a water-solubilizing group, such as sulfonate, sulfate, carboxylate, hydroxyl, amino, ammonium and the like, to enhance the solubility or transport of the control agent. In other aqueous applications of this invention, it is preferred that the control agent have ampluphilic or hydrophobic substituents, to promote to control agent migration to interfaces, or to inhabit aqueous diffusion of the control agent.

Without wanting to be bound by any particular theory, it is believed that the concentration of free radical control agent during the polymerization process, i.e., free nitroxide radical, is important to achieve a balance between controlling the polymerization reaction on one side and the reaction proceeding within a reasonably commercial time frame and with suitable monomer conversion percentages on the other side. In practical terms, the amount of control agent present in the polymerization reaction mixture should be enough to impart living type polymerization kinetics to the system, but not so much so that the polymerization reaction shuts down. Others have stated in connection with a TEMPO controlled system that rate of monomer conversion is controlled by the excess of nitroxide in the polymerization reaction mixture. See Georges et al., "The Stable Free-Radical Polymerization Process: Role of Excess Nitroxide," *Controlled Radical Polymerization* (ACS Symposium Series #685, 1998), pp. 170–179, incorporated herein by reference.

Thus, in this invention, it is preferred that the amount of free radical control agent remains relatively constant but non-zero during the polymerization. Since a certain statistical fraction of "living" polymer control chains will terminate during any radical polymerization reaction, the free radical control agents useful in this preferred embodiment should have a mechanism available that destroys the free radical either through a decomposition reaction or a neutralization reaction. In this context, the phrase "decomposition reaction" refers to the free radical control agent reacting with itself or with another free radical control agent to yield a product or products that does not have a free radical or is not a stable free radical. Similarly, in this context, the phrase "neutralization reaction" refers to the free radical control agent reacting with a reagent added to the polymerization reaction that removes or destroys the free radical associated with the control agent. In some embodiments, the X moiety allows the free radical to destabilize itself (i.e., a decomposition reaction) so that the control agent has a limited lifetime, or is destabilized by the addition of a reagent (i.e., a neutralization reaction). The useful range of stable free radical concentration depends on the exact polymerization conditions, monomers and nitroxides, but typically is in the range of from about $10^{-4}$ to $10^{-8}$ moles per liter.

Another function of control agent structure in the heterogeneous aqueous polymerization mixtures of the invention is to influence the partitioning and concentration of control agent in the various phases of the mixture, such as the water phase, polymer phase, and or monomer phase, if present. Depending on the exact polymerization conditions, this partitioning can be important to the rates and living nature of polymerization at the intended locus of polymerization as well as other locations within the heterogeneous mixture.

In more specific embodiments, each $R^1$, $R^2$ and $R^3$ is independently selected from a group consisting of alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl and silyl. Specific examples of $R^1$, $R^2$ and $R^3$ are methyl, ethyl, propyl, butyl, cyclopentyl, cyclohexyl, cyclooctyl, phenyl, benzyl, trimethylsilyl, those specific moieties listed in the above definitions and the like. In alternative embodiments, $R^1$, $R^2$ or $R^3$ may include a water-solubilizing group, such as $SO_3G$, where G is Na, K and the like. In a preferred embodiment, $R^1$ is an aryl (such as phenyl), $R^2$ is an alkyl (such as isopropyl) and $R^3$ is either an alkyl or a heteroalkyl (such as tert-butyl or $Me_3SiOCH_2(CH_3)_2C$—). In an alternative preferred embodiment, $R^1$ is an aryl (such as phenyl), $R^2$ is a cycloalkyl (such as cyclohexyl or cyclopentyl) or a tertiary alkyl (such as tert-butyl) and $R^3$ is either a tertiary alkyl or a heteroalkyl (such as tert-butyl or $Me_3SiOCH_2(CH_3)_2C$—). In still another preferred embodiment, $R^1$ is a substituted alkyl (such as $NC(CH_3)_2C$—) and $R^2CNR^3$ form a cyclic ring structure.

In one embodiment of the heterogeneous aqueous polymerization process of this invention, the control agent in radical form is combined with water, initiator, at least one monomer and optionally a surfactant, an accelerator and/or a reagent to react with the control agent under polymerization conditions. In other embodiments, the control agent is generated in situ. In one such embodiment, the control agent is added to the mixture in the form of an adduct characterized by the general formula:

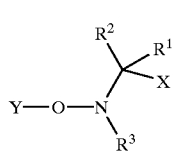

(II)

where $R^1$, $R^2$, $R^3$ and X have the above meanings, while Y is a residue capable of initiating free radical polymerization upon homolytic cleavage of the Y—O bond, including, for example, alkyl, substituted alkyl, alkoxy, substituted alkoxy, heteroalkyl, substituted heteroalkyl, aryl, and substituted aryl residues. Use of such adducts can eliminate concerns about the speed of initiation of polymer chains, effectively initiating all polymer chains at the same time upon addition of the adduct to the monomer under polymerization conditions. When the adduct is employed, the ratio of control agent to initiator can be adjusted by the addition of free radicals from any source, including, for example, additional free radical control agent (such as shown in connection with formula I, above), additional free radical initiators or radicals derived from other reactions. The adducts may be prepared by methods known in the art, such as disclosed in WO 99/03894, which is incorporated herein by reference. In another such embodiment, the control agent is generated in situ from the nitrone precursor, as is also discussed below and in WO 99/03894. In another embodiment, the adducts useful in this invention encompass compounds having monomer, oligomer or polymer disposed between the Y residue and the oxygen atom of the adduct, as shown in formula III, below. Thus, embodiments including compounds of the structure shown in formula II are within the definition of "adduct" as that term is applied to the invention.

Polymerization conditions include a temperature in the range of from about 0° C. to about 300° C., preferably between about 0° C. and about 200° C., more preferably between about 20° C. and about 150° C., and most preferably between about 20° C. and about 100° C. Polymerization conditions also include a pressure between about ambient pressure up to about 100 atmospheres. The atmosphere above the heterogeneous polymerization mixture may also be one of the polymerization conditions, and the atmosphere may be air, nitrogen, argon or another suitable atmosphere. Polymerization conditions also include the time for reaction, which may be from about 0.1 hours to about 72 hours, preferably in the range of from about 0.5 hours to about 24 hours, more preferably in the range of from about 1 hour to about 12 hours.

Initiators useful in this invention include both water-soluble initiators and solvent-soluble or monomer-soluble initiators. Generally, in some embodiments, the initiator can be capable of producing the radical fragment (Y.) that initiates radical polymerization of a monomer. Thus, an oligomer or polymer (or adduct) of this invention may be characterized by the formula:

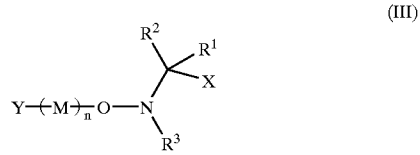

(III)

where $R^1$, $R^2$, $R^3$, Y and X have the above meanings (Y may also be derived from the list of initiators discussed below); M is one or more monomer units selected from the group consisting of styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate and combinations thereof; and n is an integer that may be zero, 1 or greater than 1. Thus, for example, when n equals 1, the compounds meeting formula III may be considered an adduct capable of initiating the free, radical polymerizations of the invention.

It is frequently convenient to generate the Y radical in the presence of monomer and control agent, and to isolate an adduct of formula III where n is 1 (but may be 2 or 3). This is an isolable compound (which may be generated in an emulsion or separately from the emulsion and later added to the emulsion) that can be easily purified and used in subsequent polymerization processes of the invention.

In general, suitable radical initiators (from which the Y residue may be derived) include any thermal, redox or photo initiators, including, for example, alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, azo compounds and halide compounds. Specific initiators include cumene hydroperoxide (CHP), t-butyl hydroperoxide (TBHP), t-butyl perbenzoate (TBPB), sodium carbonateperoxide, benzoyl peroxide (BPO), lauroyl peroxide (LPO), methylethylketone peroxide 45%, potassium persulfate, ammonium persulfate, 2,2-azobis(2,4-dimethyl-valeronitrile) (VAZO®-65), 1,1-azobis(cyclo-hexanecarbonitrile) (VAZO®-40), 2,2-azobis(N,N'-dimethyleneisobutyramidine) dihydrochloride (VAZO®-044), 2,2-azobis(2-amidino-propane) dihydrochloride (VAZO®-50) and 2,2-azobis(2-amido-propane) dihydrochloride. Redox pairs such as persulfate/sulfite and Fe(2+)/peroxide are also useful.

Surfactants can be useful in the processes and compositions of the invention. Suitable surfactants include any species or mixture of species capable of stabilizing colloidal emulsions. Generally surfactants are amphiphilic molecules comprising both hydrophobic and hydrophilic regions, which are capable of adsorbing to surfaces. Surfactants may be small molecules or polymers, micelle forming or non-micelle forming and may be anionic, cationic, zwitterionic or nonionic. In some embodiments, it may be desirable to use mixtures of surfactants, for example to enhance particle stability or control particle formation. Surfactants can play an important role in determining particle size, particle distribution, particle formation and the stability of the resulting polymer emulsion, which are factors that those of skill in the art typically consider when choosing a surfactant for any specific embodiment. Economic factors may also be considered in choosing surfactants for a particular application. Typical amounts of surfactants range from about 0.01 to about 200% by weight relative to the monomer, with a more preferred range being from about 0.1 to about 5% by weight and more specifically preferred being from about 0.1 to about 2% by weight. Polymerizable surfactants can be used. In some embodiments, however, no surfactant is required, for example, where the monomer, initiator and/or control agent are functionalized to provide "surfactant-like" properties appropriate for the particular application.

Suitable surfactants include anionic, small molecule surfactants including substituted or unsubstituted hydrocarbyl sulfates, sulfonates, carboxylates, phosphonates and phosphates, having between 6 and 30 carbon atoms per anionic functional group. When the hydrocarbyl group is substituted, it may have one or more hydrogen or carbon atoms replaced with another atom selected from the group consisting of N, S, O, Si, F, Cl, Br and I. The hydrocarbyl may also have one or more hydrogen or carbon atom replaced with a functionality such as a keto, ester, amide, ether, thioether and the like. Specific examples of anionic, non-polymeric surfactants include sodium dodecyl sulfate, sodium dodecylbenzene sulfonate, $C_{14}$–$C_{16}$ α-olefin sulfonate, oleoyl methyltaurine, alkyl sulfosuccinate, sodium stearate, alkyl substituted disulfonated diphenyloxide and nonylphenoxy oligo(ethylene glycol) sulfate. Ionic polymers can be used, including polyethyleneimine, polyacrylic acid, carboxymethyl cellulose and the like. Suitable cationic surfactants include cetyltrimethyl ammonium bromide, N-methyl-(4-dodecylpyridinium bromide). Suitable nonionic surfactants include random and block copolymers of polyvinyl alcohol, polyvinylacetate co-polyvinyl alcohol, polyethyleneoxide co-buyleneoxide, polyethyleneoxide-co-propyleneoxide, polyalkyl-glycidol, substituted polyalkyl-glycidol. In other embodiments, useful surfactants include, for example, ethoxylated mono-, di- and trialkylphenols (degree of ethoxylation: 3 to 100, alkyl radical: $C_4$ to $C_{12}$), ethoxylated fatty alcohols (degree of ethoxylation: 3 to 100, preferably 6 to 50, alkyl radical: $C_6$ to $C_{20}$) and alkali metal and ammonium salts of alkylsulfates (alkyl radical: $C_8$ to $C_{18}$), of sulfuric half-esters of ethoxylated alkanols (degree of ethoxylation: 1 to 70, in particular 2 to 10, alkyl radical: $C_{10}$ to $C_{18}$) and of ethoxylated alkylphenols (degree of ethoxylation: 3 to 100, preferably 6 to 50, alkyl radical: $C_4$ to $C_{18}$) and alkali metal and ammonium salts of alkanesulfonic acids (alkyl radical: $C_{10}$ to $C_{18}$) and of alkylarylsulfonic acids (alkyl radical: $C_9$ to $C_{18}$). Further suitable surfactants, such as sulfosuccinates, are described in Houben-Weyl, Methoden der organischen Chemie, Volume XIV/1, Makromolekulare Stoffe, Georg-Thieme Verlag, Stuttgart, 1961, pages 192 to 208. Alternative surfactants include functional monomers, polymerizable surfactants and water-soluble surface-active polymers, including block copolymers. Specific examples include polyvinyl alcohols, cellulose derivatives or vinylpyrrolidone-containing copolymers. A detailed description of further suitable protective colloids is given in Houben-Weyl, Methoden der organischen Chemie, Volume XIV/1, Makromolekulare Stoffe, Georg-Thieme-Verlag, Stuttgart, 1961, pages 411 to 420. Currently commercially available surfactants that are useful in this invention are listed below in Table 1.

TABLE 1

| Trade Name | Supplier | Contents |
|---|---|---|
| Ionics | | |
| Abex VA-50 | Rhodia | 46%; 1:1 mix of anionic and ethoxylated octyl phenol |
| Abex 2020 | Rhodia | Anionic/non-ionic mix (APE free), 30% |
| Abex 2030 | Rhodia | Anionic/non-ionic mix (APE free), 30% |
| Abex 18-S | Rhodia | Na Ether Sulfates; APE-free, 35% |
| Abex 12-S | Rhodia | Na Ether Sulfates; APE-free, 30% |
| Aerosol OT | Sigma | [(Bis-2-ethylhexyl)sodium sulfosuccinate, $C_{20}H_{37}O_7S.Na$, $M_w$ 444.6, 10% |
| Aerosol 22 | Sigma | [(Bis-2-ethylhexyl)sodium sulfosuccinate, $C_{20}H_{37}O_7S.Na$, $M_w$ 444.6, neat d = 1.12 |
| Calfax DB-45 | Pilot Chemical | $C_{12}$(branched) Sodium diphenyloxide disulfonate, 45% |
| Calfax 16L-35 | Pilot Chemical | $C_{16}$(linear) Sodium diphenyloxide disulfonate, 35% |
| Calimulse L-30 | Pilot Chemical | Sodium linear alkyl benzene sulfonate 30% |
| Calimulse EM-30 | Pilot Chemical | Sodium branched dodecyl benzene sulfonate 30% |

TABLE 1-continued

| Trade Name | Supplier | Contents |
|---|---|---|
| Calsoft F-90 | Pilot Chemical | Sodium linear alkyl benzene sulfonate, solid, 90+% |
| Dowfax C6L | Dow | Disulfonated diphenyloxide with $C_6$ backbone |
| Dowfax C10L | Dow | Disulfonated diphenyloxide with $C_{10}$ backbone |
| Dowfax 8390 | Dow | Disulfonated diphenyloxide with $C_{16}$ backbone, 45% |
| Emulgator 825 | BASF | anionic/non-ionic mix |
| Emulgator 825-S | BASF | anionic/non-ionic mix |
| Rhodacal A-246/L | Rhodia | sodium alpha C–C16 olefin sulfonate (38–41%) |
| Rhodacal DS-4 | Rhodia | sodium dodecyl benzene sulfonate 23% |
| SDS | Aldrich | sodium dodecyl sulfate |
| SDBS | Aldrich | sodium dodecyl benzene sulfonate 90% |
| Triton QS-30 | Union Carbide | 90%, gel like |
| Triton X-200 | Union Carbide | 28% aq dispersion |
| Atphos 3232 | ICI | Polyoxyethylene phosphate ester |
| Atphos 3226 | ICI | anionic sfac, phosphoric acid |
| Atphos 3202 | ICI | NonylPE n = 6, acid form, 100% |
| Nonionics | | |
| Abex 2545 | Rhodia | |
| Abex 2535 | Rhodia | |
| Dynol 604 | Air Products | Ethoxylated acetylenic diols, 100% |
| Igepal CO-210 | Aldrich | APE ($C_9H_{19}$—$C_6H_4$—$(OCH_2CH_2)_2OH$) 100% |
| Igepal CO-520 | Aldrich | APE ($C_9H_{19}$—$C_6H_4$—$(OCH_2CH_2)_5OH$) 100% |
| Igepal CA-897 | Rhodia | APE (octylphenol ethoxylate) 70%, n = 40 |
| Igepal CO-897 | Rhodia | APE (nonylphenol ethoxylate) 70% n = 40 |
| Pluronic F38 | BASF | EO-PO-EO block, average $M_w$ 4700 HLB 31 |
| Pluronic F98 | BASF | EO-PO-EO block, average $M_w$ 13K, HLB 28 |
| Pluronic P65 | BASF | EO-PO-EO block, average $M_w$ 3400 HLB 17 |
| Surfynol 104 PA | Air Products | 50% in isopropyl alcohol, 50% 2,4,7,9-tetramethyl-5-decyne-4,7,-diol |
| Surfynol 104 PG-50 | Air Products | 50% in propylene glycol, 50% 2,4,7,9-tetramethyl-5-decyne-4,7,diol |
| Surfynol DF-58 | Air Products | silicone-based |
| Surfynol 440 | Air Products | Surfynol 104 with ethylene oxide chains, more hydrophilic, 100% |
| Surfynol 465 | Air Products | Surfynol 104 with ethylene oxide chains, more hydrophobic, 100% |
| Triton X-100 | Union Carbide | t-octylphenoxy-polyethoxyethanol (n = 9.5), 100% |
| Triton X-405 | Union Carbide | t-octylphenoxy-polyethoxyethanol, 70% |

Monomers that may be polymerized using the methods of this invention (and from which M may be derived) include at least one monomer selected from the group consisting of styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate and combinations thereof. Functionalized versions of these monomers may also be used. Specific monomers or comonomers that may be used in this invention and from which M is derivable include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylaminostyrene (all isomers), α-methylvinyl benzoic acid (all isomers), diethylamino α-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, butadiene, isoprene, chloroprene, ethylene, vinyl acetate, 2-(2-oxo-1-imidazolidinyl)ethyl 2-methyl-2-propenoate, 1-[2-[[2-hydroxy-3-(2-propyl)propyl)]amino]ethyl]-2-imidazolidinone, W-vinyl pyrrolidone, N-vinyl imidazole, crotonic acid, vinyl sulfonic acid, and combinations thereof.

Suitable accelerators useful in this invention include alkylating and acylating agents, Lewis Acids, ketones, aldehydes, anhydrides, acid esters, imides, oxidants and reducing agents. Specific accelerators include acetic acid, acetic anhydride, camphor sulfonic acid, acetole (1-hydroxyacetone) and the like. Other accelerators useful herein are recited in Hawker et al., "Development of a New Class of Rate-Accelerating Additives for Nitroxide-Mediated 'Living' Free Radical Polymerization," *Tetrahedron*, Vol. 53, No. 45, pp. 15225–15236 (1997), which is incorporated herein by reference.

The ratios of components (e.g., initiators, surfactants, monomers, accelerators and control agents) in the polymerization mixture may be important and can vary widely depending on the particular application. The ratio of monomer to initiator can be used to determine the molecular weight of polymers produced using the controlled heterogeneous free radical polymerization processes of the invention. According to these processes, the weight average molecular weight of the resulting polymers depends linearly on the number of free radical chains in the polymerization and the mass of monomer. Assuming every initiator initiates one chain, the selection of a monomer to initiator ratio provides an opportunity to "dial in" to a desired molecular weight (or degree of polymerization) (taking into account the ratio of chains formed to initiating fragments formed by the particular initiator in question).

In typical embodiments, the monomer to initiator ratio may be in the range of from about 10:1 to about 10,000:1, more preferably the range of from about 50:1 to about 10,000:1 and most preferably the range of from about 100:1 to about 5000:1. Another ratio that may be controlled is the ratio of equivalents of initiator to free radical control agent, (with the assumption that the amount of initiator is approximately equivalent to the number of radical produced), which is typically in the range of from about 1:0.1 to about 1:4, more preferably the range of from about 1:0.3 to about 1:2 and most preferably the range of from about 1:0.4 to about 1:1.6. When an accelerator is present the ratio of free radical control agent to accelerator is typically in the range of from about 1:0.1 to about 1:4, more preferably the range of from about 1:0.3 to about 1:2 and most preferably the range of from about 1:0.4 to about 1:1.6. The surfactant to monomer ratio may be controlled and is typically in the range of from about 0.0001 to about 2:1, more preferably the range of from about 0.001:1 to about 0.05:1 and most preferably the range of from about 0.001:1 to about 0.02:1 (although for some emulsions there may be no surfactant added at all where other reaction components perform that function). The percent solids may be in the range of from 0.001% to about 90% by volume. In some preferred applications, the novel aqueous polymer emulsions are produced with a solids content of greater than or equal to 40, advantageously greater than or equal to 50%, by volume, based on the total aqueous polymer emulsion. The useful solids content for other applications is from 0.5 to 95% by volume. The preparation of the novel aqueous polymer emulsions is carried out according to the product by process definition of the subject according to the invention, as stated at the outset, i.e., by the free radical aqueous emulsion polymerization method in the presence of dispersants and free radical polymerization initiators. The ratio of the aqueous phase to the total amount of the monomers used in both stages is chosen according to the desired solids content of the aqueous polymer emulsion to be prepared.

In the broadest sense, an emulsion polymerization is any heterogeneous polymerization in an aqueous environment. Typically, these systems produce particles of polymer as product. Those skilled in the art recognize many variants of these polymerizations, with typical classifications distinguishing between polymerizations occurring in true emulsions, micro emulsions, mini emulsions, suspensions and dispersions. These processes are generally distinguished by differences in process, components or results, with specific factors including the presence, amount and type of surfactant required; presence, amount and type of intitiator; presence, type and amount of monomer, including monomer solubility; polymerization kinetics; temperature; order of addition of the components, including the timing of addition of the components (e.g., monomer); solubility of the polymeric product; agitation; presence of cosolvents; resulting particle size; particle stability in the polymerization system toward coagulation or sedimentation; and other factors known to those skilled in the art.

The systems of the invention may not fall completely into any of the traditional definitions typically applied by those skilled in the art (e.g., true emulsions vs. micro emulsions). These systems may fall between the traditional definitions, while having properties characteristic of one or many traditionally-classified systems. Accordingly, the polymerizations of the invention can be considered to encompass traditional (or true) emulsion polymerizations, micro and mini emulsions as well as to suspension and dispersion polymerizations. Characteristics that can be used to distinguish these heterogeneous polymerization systems are set out in Table 2, below.

TABLE 2

| Property | Traditional Emulsion | Mini Emulsion | Micro Emulsion | Suspension | Dispersion |
|---|---|---|---|---|---|
| Locus of polymerization | particles | droplets | particles | droplets | water |
| Distribution of monomer | droplets/particles | droplets | particles | droplets | droplets/water |
| Distribution of polymer | particles | droplets | particles | droplets | particles |
| Aqueous solubility of monomer | moderate to high | low to moderate | moderate | low to moderate | high |
| Importance of agitation | moderate to low | high (at start) | low | high | high |
| Typical resulting particle size | 10 to 200 nm | 50 to 500 nm | 10 to 100 nm | 500 to 5000 nm | 500 to 5000 nm |
| Typical particle size distribution | narrow | broad | narrow | broad | broad |
| Typical amount of surfactant (relative to monomer) | 0 to 5% | 0.1 to 10% | ≈100% | 0 to 5% | 0 to 5% |
| Thermodynamic stability of particles before polymerization | not stable | not stable | stable | not stable | not stable |
| Typical maximum solids content | 50% | 20% | <10% | 40 to 50% | 40 to 50% |

Some of these ranges are subjective and extremes may often only be obtained in exceptional circumstances. Terms such as low, medium and high are subjective, and are intended to illustrate differences in the classifications known to those skilled in the art. The processes of the invention are distinguished as discussed herein.

One specifically preferred embodiment of the invention is a controlled heterogenous polymerization reaction in an emulsion characterized by particle sizes ranging from 20 to 300 nm, and preferably from 30 to 200 nm or from 40 to 140 nm. Polymerizations of this embodiment may have process parameters similar to those discussed above for "traditional" or "true" emulsion polymerizations. These emulsions are stable (on the order of many months with no observed coagulation or sedimentation, yet are prepared using surfactant in amounts less than 2% by weight to monomer. These emulsions feature a uniform distribution of particle sizes (nonuniformity of the polymer particle diameter distribution—e.g., R.M.S. variation in average polymer particle diameter of less than about 50%).

The controlled particle sizes that characterize the controlled polymer emulsions of some embodiments of the invention provide a number of benefits in many applications. The living nature of the polymerization processes of the invention allow for novel means for controlling particle size and distribution of the resulting polymer emulsions. Emulsions of smaller particles are generally very stable and have useful process advantages such as faster reaction kinetics and more scalable and reproducible preparations. Such emulsions have useful optical properties (e.g., lower turbidity), high viscosity, greater surface area and coalesce to form more uniform or thinner films, all of which may be advantageous in typical applications such as adhesives, dispersants, coatings and separation media. In other embodiments directed to different applications, larger particles may be desirable and can be obtained using the heterogeneous aqueous free radical polymerizations of the invention. Desirable properties of large-particle emulsions include opacity, low viscosity, and ease of polymer isolation. Emulsions with uniform or broad particle size distribution can result from processes of the invention, with various advantages of particle size distribution known to those skilled in the art. For example, broad particle size distribution may result from properly chosen polymerization conditions, or may be obtained by blending particles of narrow size distribution obtained from several different polymerizations.

The use of nitroxide control agents under emulsion conditions offers other benefits associated with living kinetics (e.g., linear increase in molecular weight as a function of conversion). The controlled free radical emulsion polymerizations of the invention provide a high degree of control over molecular weight, especially at high molecular weight, (as high as $\geq 50,000$, or even $\geq 100,000$), often with narrow molecular weight distribution (polydispersity ($M_W/M_N$) generally less than 2 and preferably between 1.1 and 1.8). Likewise, nitroxide control agents provide significant control of particle sizes. While typical particle sizes for uncontrolled radical emulsion polymerizations range from 50 to about 200 nm depending on the amount of monomer and surfactant, polymerizations of the invention have been shown to provide emulsions with much smaller particle size, under similar condition of surfactant and monomer concentration. For example, uncontrolled emulsion polymerizations of n-butylacrylate (1% surfactant, 20% solids and target $M_w$ of 100,000) yield particle sizes that range from about 100 to about 150 nm. By contrast, upon adding 0.8 equivalents of control agent to initiator, particle sizes are obtained in the range of 50–60 nm, with markedly lower emulsion turbidity reflecting decreasing particle size as the amount of control agent is increased.

This invention also is directed toward a process for polymerization that allows the effective use of organic soluble initiators and otherwise slow initiators in a heterogeneous aqueous polymerization process that has living type kinetics. Typically, initiation in a living type polymerization system must be very fast so that most of the polymer chains are propagating at the same time. If an initiator is too slow in its creation of radicals, then new radical chains may be created during the propagation of other chains, leading to broadened molecular weight distributions (or polydispersities or weight average molecular weight over number average molecular weight or $M_w/M_n$). Also, organic soluble initiators are not typically used in a batch emulsion polymerizations (as opposed to semi-continuous or continuous polymerizations) because they may reside in and initiate polymerization in the monomer pools (or droplets), which may lead to loss of control, large particle sizes, unstable emulsions, undesirable polymerization in the monomer pools (and related issues, such as bimodal or multi-modal polydispersities). This process overcomes these potential problems by taking advantage of the living type kinetics of the polymerization mixtures of this invention (including the ability to re-initiate chains) by supplying the monomer to the system in at least two stages. In the first stage, the water, surfactant, control agent and initiator are combined with a fraction of the total amount of monomer. This combination is mixed for a predetermined period of time at a predetermined temperature. Since the amount of monomer is limited, the polymerization reaction proceeds until the monomer is used up, effectively creating, "living" oligomers that can be re-initiated. In this manner, an otherwise slow initiator is given the time it needs to initiate as many chains as it can and an organic-soluble initiator cannot cause polymerization outside of the desired control mechanism. The amount of time and/or the temperature for this first step is chosen so that the chosen initiator is substantially completely reacted prior to the second step of the process. The second step is the addition of the remainder of the monomer (with or without other components), which continues the propagation. Additional steps can be added for different monomers to create block copolymers, such as di-block, tri-block or higher order block polymers, or to prepare telechelic polymers or macromonomers.

In performing this process, the time and temperature of the first step is dependent on the choice of initiator and monomer. In this first step, the ratio of monomer to initiator is typically chosen based on the desired molecular weight of the polymer chains, and may typically fall in the molar range from about 10:1 to about 1000:1 and preferable in the range of from about 10:1 to about 500:1. Typically, the first step is carried out for between about 0.5 hours to 20 hours, preferably between about 1 and 15 hours. Also typically, the first step is carried out at a temperature of between about 50° C. and 200° C., preferably between about 70° C. to about 90° C. Each of the "living" oligomers may be characterized by above formula III, where n is a relatively low integer, such as between about 1 and 100.

The living nature of the polymerization processes of this invention provide those of skill in the art the ability to create virtually any type of polymer architecture desired as well as selection from a wide variety of monomers. Thus, this invention includes novel block copolymers of styrene and acrylic acid; styrene and acrylamides (such as t-butyl acrylamide and dimetyl acrylamide); styrene and acrylates (such as n-butyl acrylate and ethyl acrylate); styrene and methacrylates (such as n-butyl methacrylate and methyl methacrylate); acrylic acid and methacrylic acid; acrylic acid and acrylamides; acrylic acid and acrylates; acrylic acid and methacrylates; methacrylic acid and acrylamides; methacrylic acid and acrylates; methacrylic acid and methacrylates; acrylamides and acrylates; acrylamides and methacrylates; and acrylates and methacrylates. Some of these block copolymers are exemplified in the below examples. Although some of these types of block copolymers may have been prepared by other methods, this invention provides a controlled free radical method of synthesis with living type kinetics that leads to novel properties. Novel properties include higher molecular weights (e.g., above 50,000 weight average molecular weight) and better particle size control, as discussed above. From these properties, other properties can be derived, as discussed elsewhere in this specification. For some applications, the polymers may be used in the heterogeneous medium in which they are created; in others, the polymers may be isolated from the emulsion. Polymers may be isolated using a variety of well-known techniques, including, for example, coating, drying, spray drying, coagulation, extrusion, addition of solvent, chemical modification of the polymer and the like, depending on the application. Modifiers, stabilizers or other additives may be added to the polymers for particular applications, whether in emulsion or not, as is known to those of skill in the art.

As used herein, "block copolymer" refers to a polymer comprising at least two segments of differing composition; having any one of a number of different architectures, where the monomers are not incorporated into the polymer architecture in a solely statistical or uncontrolled manner. Although there may be three, four or more monomers in a single block-type polymer, architecture, it will still be referred to herein as a block copolymer. In some embodiments, the block copolymer will have an A-B architecture (with "A" and "B" representing the monomers). Other architectures included within the definition of block copolymer include A-B-A, A-B-A-B, A-B-C, A-B-C-A, A-B-C-A-B, A-B-C-B, A-B-A-C (with "C" representing a third monomer), and other combinations that will be obvious to those of skill in the art.

In another embodiment, the block copolymers of this invention include one or more blocks of random copolymer together with one or more blocks of single monomers. Thus, a polymer architecture of A-R, A-R-B, A-B-R, A-R-B-R-C, etc. is included herein, where R is a random block of monomers A and B or of monomers B and C. Moreover, the random block can vary in composition or size with respect to the overall block copolymer. In some embodiments, for example, the random block R will account for between 5 and 80% by weight of the mass of the block copolymer. In other embodiments, the random block R will account for more or less of the mass of the block copolymer, depending on the application. Furthermore, the random block may have a compositional gradient of one monomer to the other (e.g., A:B) that varies across the random block in an algorithmic fashion, with such algorithm being either linear having a desired slope, exponential having a desired exponent (such as a number from 0.1–5) or logarithmic. The random block may be subject to the same kinetic effects, such as composition draft, that would be present in any other radical copolymerization and its composition, and size may be affected by such kinetics, such as Markov kinetics. For example, as shown below in the examples, a block copolymer of (random styrene-acrylic acid) and n-butylacrylate is made that is within the scope of this definition. Any of the monomers listed elsewhere in this specification may be used in the block copolymers of this invention.

A "block" within the scope of the block copolymers of this invention typically comprises about 10 or more monomers of a single type (with the random blocks being defined by composition and/or weight percent, as described above). In preferred embodiments, the number of monomers within a single block is about 15 or more, about 20 or more or about 50 or more. However, in an alternative embodiment, the block copolymers of this invention include blocks where a block is defined as two or more monomers that are not represented elsewhere in the copolymer. This definition is intended to encompass adding small amounts of a second monomer at one or both ends of a substantially homopolymeric polymer. In this alternative embodiment, the same copolymer architectures discussed above apply. This definition is therefore intended to include telechelic polymers, which include one or more functional end groups capable of reacting with other molecules. Thus, generally, a telechelic polymer is a block copolymer with in the definitions of this invention. The functional groups present at one or both ends of a telechelic polymer may be those known to those of skill in the art, including, for example, hydroxide, aldehyde, carboxylic acid or carboxylate, halogen, amine and the like, which have the ability to associate or form bonds with another molecule. Likewise, the block copolymers of the invention are intended to encompass telechelic polymers containing bifunctional groups, such as allyl-terminated or vinyl-terminated telechelics, sometimes referred to as macromonomers or macromers because of their ability to participate in polymerization reactions through the terminal functional group.

Combining the above embodiments provides a particularly powerful method of designing block copolymers. For example, a block copolymer may have the architecture F-A-B-F, where F represents functional groups that may be the same or different within a single F-A-B-F structure (which, therefore, may encompass F-A-B-F'). Other block copolymer architectures within the scope of this invention include A-R-B-F and F-A-R-B-F. Other architectures will be apparent to those of skill in the art upon review of this specification—indeed, without wishing to be bound by any particular theory—it is the living nature of the emulsions of this invention that provide the ability to even make these novel block copolymers.

In one embodiment, block copolymers are assembled by the sequential addition of different monomers or monomer mixtures to living polymerization reactions. In another embodiment, the addition of a pre-assembled functionalized block (such as a telechelic oligomer or polymer) to a living free radical polymerization mixture yields a block copolymer. Ideally, the growth of each block occurs with high conversion. Conversions are determined by size exclusion chromatography (SEC) via integration of polymer to monomer peak. For UV detection, the polymer response factor must be determined for each polymer/monomer polymerization mixture. Typical conversions can be 50% to 100% for each block. Intermediate conversion can lead to block copolymers with a random copolymer block separating the two or more homopolymer blocks, depending on the relative rates of polymerization and monomer addition. At high conversion, the size of this random block is sufficiently small such that it is less to affect polymer properties such as phase separation, thermal behavior and mechanical modulus. This fact can be intentionally exploited to improve polymerization times for many applications without measurably affecting the performance characteristics of the resulting polymer. This is achieved by intentionally "killing" or terminating the living nature of the polymerization when a desired level of conversion (e.g.,>80%) is reached by neutralizing the control agent, for example by introducing acids, bases, oxidizing agents, reducing agents, radical sources, scavengers, etc. In the absence of control agent, the polymerization continues uncontrolled (typically at much higher reaction rates) until the remaining monomer is consumed. Block copolymer can also be created by grafting monomers, monomer mixtures, oligomers or polymers only polymers having multiple available functional groups.

In other embodiments, block copolymers can be prepared by grafting processes, preparation of telechelis polymers, preparation of macromonomers, etc. In these embodiments, at least one polymer segment is derived from a living or controlled process of the invention, while other segments can be derived from any polymerization process, including, for example, controlled or uncontrolled radical polymerization, condensation polymerization, ionic polymerization, surface modification or grafting, or other addition or step-growth processes.

The combination of heterogeneous (and particularly emulsion) conditions with living-type free radical kinetics provides a high degree of control over the composition, architecture, phase morphology and microstructure of polymers produced according to the invention. These methods may be practiced to form new polymers, including, for example, di-, tri-, poly-, multi-arm, star and graft block copolymers in addition to novel homopolymers.

Block copolymers allow the combination of potentially diverse polymer properties (such as hard/soft and/or hydrophilic/hydrophobic (amphiphilic) blocks) into a single polymer chain. Hard/soft block copolymers combine segments with significantly different glass transition temperatures $T_g$. A typical hard/soft copolymer pairs a relatively "hard" block (e.g., styrene)with a relatively "soft" block (e.g., butyl acrylate). The resulting materials can possess performance attributes not found in any of the constituent segments. The presence of microphase separation and various phase morphologies in block copolymers is associated with unique performance attributes of many block copolymers. For example, by combining the stiffness or rigidity characteristic of hard materials with the compliance of soft materials, block copolymers may exhibit advantageous properties, such as processability under melt conditions, elasticity, resistance to abrasion and cracking and desired creep characteristics (corresponding to the material's ability to hold its shape under external stresses) depending on morphology, making them appropriate for use as extrudable bulk materials, coatings and separation media. The exact properties of a hard/soft copolymer depend significantly on the difference between the glass transition temperatures of the constituent blocks; accordingly, selection of monomers having glass transition temperatures a particular distance apart can lead to hard/soft block copolymers having particular desired characteristics. Thus, while for one application it may be appropriate to combine blocks having glass transition temperatures that differ by, for example, 20° C., the choice of $T_g$ (and therefore of materials) depends on the application. Monomers that can be combined to form hard and soft blocks are known in the art. See e.g., U.S. Pat. No. 5,755,540.

Likewise, the amphiphilic block copolymers produced according to the invention display combinations of hydrophobic and hydrophilic properties that make such materials appropriate for use as surfactants or dispersants, scavengers, surface treatments and the like. Different block sizes over all ratios of monomers and molecular weights lead to families of novel compounds, for example thermoplastics, elastomers, adhesives, and polymeric micelles.

Multi-arm or star polymers can be generated using initiators capable of initiating multiple free radical polymerizations under the controlled emulsion conditions of the invention. Such initiators include, for example polyfunctional adducts of the form:

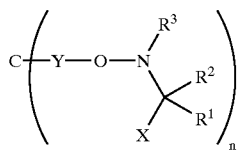

where n=2–20 and C represents a polyfunctional core molecule. Following initiation, the growth of each arm is controlled by the same living kinetics described for linear polymers, making it possible to assemble star polymers whose arms include individual homopolymers as well as di, tri or higher order block copolymers. Alternatively, multi-arm polymers are formed by growing end-functionalized oligomers or polymers followed by the addition of a cross-linking monomer such as ethylene glycol diacrylate, divinyl benzene, methylene bisacrylamide, trimetylol propane triacrylate, etc. The small hydrodynamic volume of star polymers produced according to these methods provides properties such as low viscosity, high $M_w$, and high functionality useful in applications such as rheology control, thermosets, and separation media. Similarly, the inclusion of branched or multiple ethylenically unsaturated monomers enables the preparation of graft polymers, again exhibiting the living kinetics characteristic of the emulsion polymerization of the invention.

The existence of a block copolymer according to this invention is determined by methods known to those of skill in the art. For example, those of skill in the art may consider nuclear magnetic resonance (NMR) studies of the block copolymer. Those of skill in the art would also consider the measured increase of molecular weight upon addition of a second monomer to chain-extend a living polymerization of a first monomer. Block copolymer structure can be suggested by observation microphase separation, including long range order (determined by X-ray diffraction), microscopy and/or birefringence measurements. Other methods of determining the presence of a block copolymer include mechanical property measurements, (e.g., elasticity of hard/soft block copolymers), thermal analysis and chromatography (e.g., absence of homopolymer).

Measurement of optical properties, such as absorbance (color and clarity), provides information about the phase morphology and microstructure of the polymer emulsions. Thus, for example, birefringence measurements may indicate the presence of optical anisotropy resulting from microphase separation in hard/soft block copolymers of styrene and butyl acrylate. Likewise, sharp color delineations in optical micrographs of annealed polymer films can indicate the presence of ordered, microphase-separated block copolymer structure.

Block copolymers of sufficiently high molecular weight phase separate on a microscopic scale, to form periodically arranged microdomains which typically comprise predominantly one or the other polymer. These may take the form of lamellae, cylinders, spheres, and other more complex morphologies, and the domain sizes and periods are typically in the range 10–100 nm. Such microphase separation can be detected obtained in a variety of ways, including electron microscopy, x-ray or neutron scattering or reflectivity, measurement of optical anisotropy, and rheological measurements. The absence of a periodic microstructure is not necessarily evidence against having synthesized a block copolymer, as such absence may be due to low molecular weight, weak intermolecular interactions, or inadequate time and slow kinetics for microphase separation. However, the presence of a periodic microstructure on the 10–100 nm scale is considered extremely compelling evidence for block copolymer formation in accord with this invention.

Figure 12:
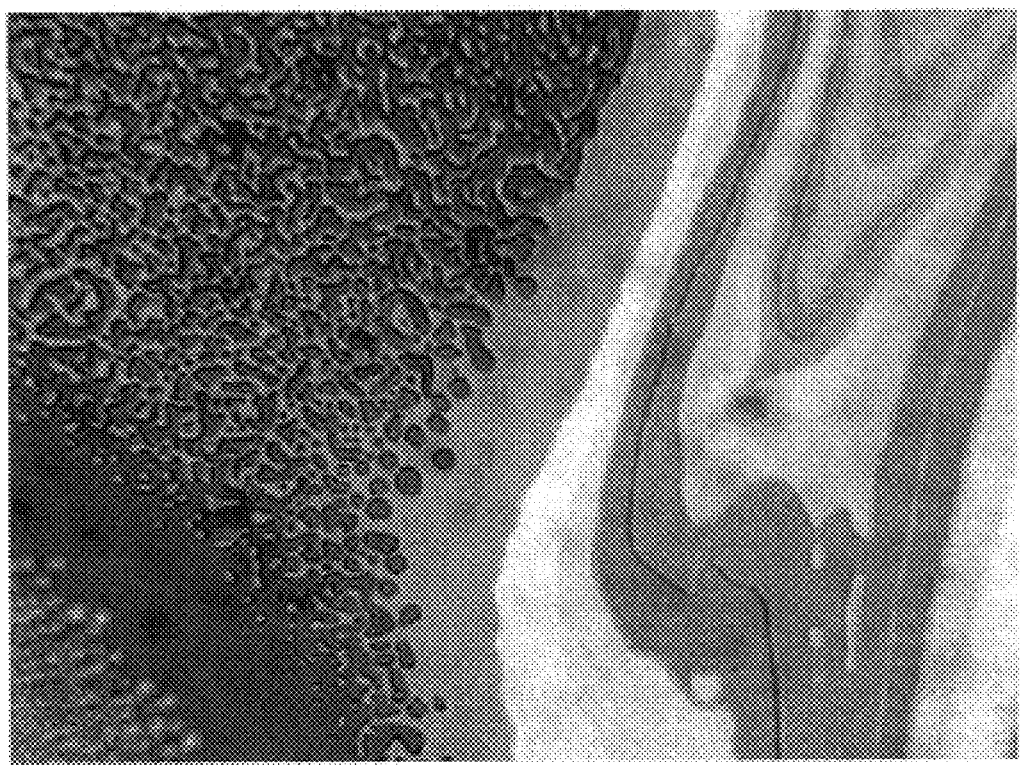
FIG. 12 is a reflection optical micrographs from copolymer emulsions synthesized according to the invention.

Block copolymers are well-known to form terraced films, where the film thickness is restricted to integer or half-integer multiples of the microstructure period. This occurs because preferential interactions of one or the other block with the substrate and/or free surface cause a layering of the microdomains parallel to the film surface (see for example G. Coulon, D. Ausserre, and T. P. Russell, *J. Phys. (Paris)* 51,777 (1990); and T. P. Russell, G. Coulon, V. R. Deline, and D. C. Miller, *Macromolecules* 22, 4600–6 (1989)). When observed in a reflection microscope (on a reflecting substrate such as a silicon wafer), the terracing manifests itself as a series of discrete, well-defined colors with sharp boundaries between them as shown in FIG. 12. The colors are a result of interference between light reflected from the top and bottom surfaces of the film, and depend on the local film thickness ("Newton's rings"). If terracing does not occur, the colors blend continuously from one into the other.

Figure 13A:
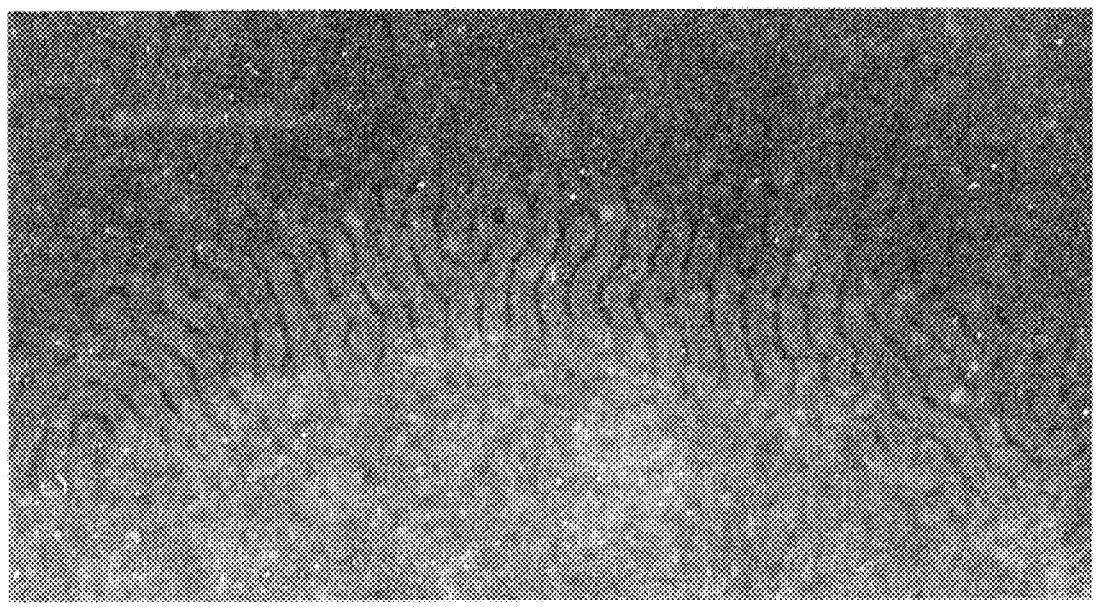
FIGS. 13A and 13B are transmission electron micrographs of a copolymer emulsion synthesized according to the invention.
Figure 13B:
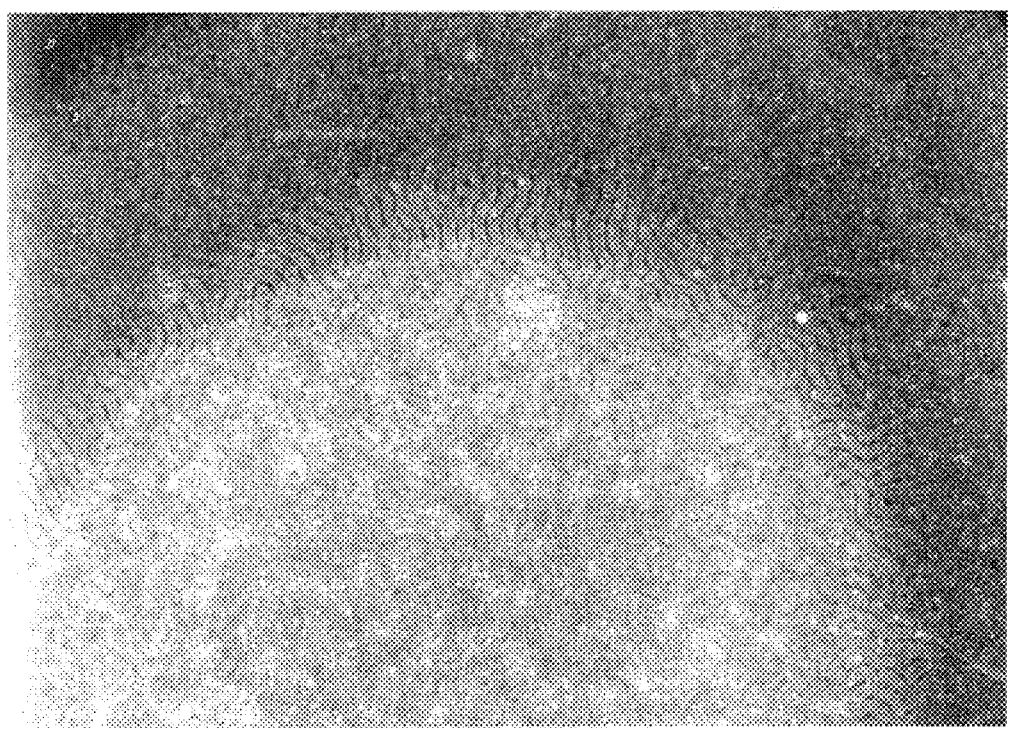

The presence of block copolymer can also be determined using transmission electron microscopy as illustrated in FIGS. 13A and 13B.

The novel properties of the copolymers and emulsions, including the high molecular weight, low polydispersity and controlled phase morphology and microstructure of the copolymers and the particle size and optical purity of the emulsions make them suitable for a wide variety of applications including adhesives, binders, coatings, dispersants, separation media, scavengers, rheology modifiers, bulk extrudable materials and health and personal care products.

EXAMPLES

Synthesis work was carried out under an inert atmosphere in a glove box under a nitrogen or argon atmosphere. All polymerization experiments were carried out in 1 mL glass vials fitted in an aluminum block, and sealed with a Teflon faced silicon rubber gasket backed with a stainless steel lid. Agitation was achieved by placing a 5 mm diameter glass ball in each vial and mounting the aluminum block on a rocking platform oscillating at one to two Hz. Heating was achieved using resistive heaters mounted in the aluminum block. The total polymerization reaction volume was 0.7 mL. The starting components for polymerizations were delivered in aqueous or monomer solutions, and typical concentrations were 0.02 to 0.1 mol/L. In general, the initiator was the last component added to the polymerizations. After the reactions had been heated for a predetermined time at a predetermined temperature, the complete contents of each reaction was dissolved in 10 mL of THF and analyzed by SEC (size exclusion chromatography) using rapid SEC/adsorption chromatography as described in commonly assigned U.S. Provisional Patent Application No. 60/080,652, filed Apr. 3, 1998, which is hereby incorporated herein by reference. Specifically, SEC was performed using a Waters 486 UV detector at 220 nm, with two 5 cm×8 mm columns in series custom packed with Suprema Gel (PSS, Mainz Germany).

Monomers were degassed by applying three freeze-pump-thaw cycles. Commercially available initiators were purchased from the suppliers listed in Table 1, above and used as is. Surfactants and any other reagents were used as received (when they were dry solids), or degassed by applying three freeze-pump-thaw cycles (when they were liquids or solutions). Unless otherwise noted, reagents were purchased from Aldrich of Milwaukee, Wis. The water used in all experiments was distilled and degassed prior to use. Degassing was accomplished by stirring the water while under dynamic vacuum and stripping off approximately 20% of the water.

Nuclear magnetic resonance spectra were recorded on a Bruker Spectrospin 300 instrument at room temperature. Thin layer chromatography was performed using 2.5×7.5 cm glass plates precoated with silica gel 60 F254 (EM Science, Merck KgaA, Darmnstadt, Germany), with, detection by UV-quenching at $\lambda$=254 nm and/or staining with 10% phosphomolydic acid hydrate in EtOH with heating. Gas chromatography/mass spectrometry (GC/MS) was performed using an HP 6890 gas chromatograph equipped with an automatic injector, a siloxane-coated capillary column, and an HP 5973 mass spectrometer.

Example 1

Preparation of Nitroxide

The following scheme 1 was followed to prepare nitroxide control agents useful in this invention. Part C of this example demonstrates preparation of a nitroxide/initiator adduct.

Scheme 1

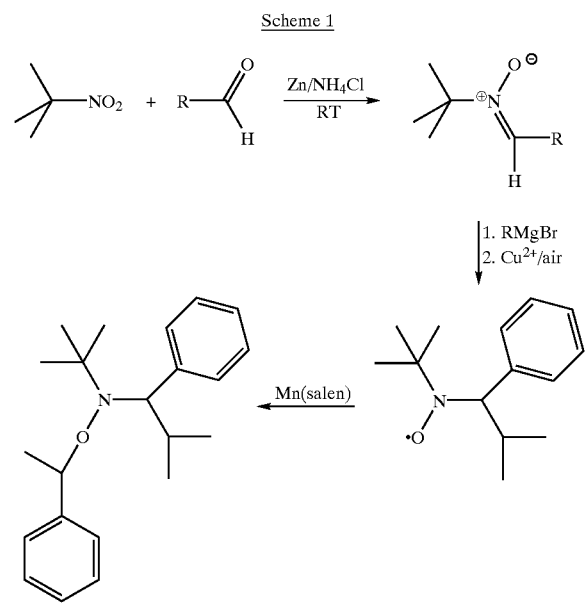

Part A: N-tert-butyl-A-isopropylnitrone

A mixture of 2-methyl-2-nitropropane (51.5 g, 500 mmol), isobutyraldehyde (36.0 g, 500 mmol), ammonium chloride (29.4 g, 550 mmol) and 1000 mL of water were cooled to 0° C. in an ice bath. 500 mL of diethyl ether was then added to partially dissolve the crystallized 2-methyl-2-nitropropane. Zinc powder (130 g, 2.00 mol) was added in small portions over 1 h upon stirring. After 8 h, the mixture was filtered through a sintered glass filter and the residue washed three times with 300 mL of methanol. The product was extracted four times with 500 mL of dichloromethane. The organic layers were combined and washed with 800 mL of brine, dried over magnesium sulfate and concentrated in vacuo to give 59.9 g (84% yield) of crude nitrone as a colorless low melting solid, partially crystallized at room temperature. TLC (10:1 EtOAc:MeOH, molybdenum stain). Rf=0.49; $^1$H NMR (250 MHZ, CDCl$_3$): D 6.52 (s, 1H), 3.10 (m, 1H), 1.42 (s, 9H), 1.11 (d, 6H); $^{13}$C NMR (63 MHZ, CDCl$_3$): D 139.55, 69.21, 30.67, 28.49, 26.10

Part B: 2,2,5-Trimethyl-4-phenyl-3-azahexane-3-nitroxide

N-tert-butyl-A-iso-propylnitrone (66.0 g, 461 mmol) was dissolved in 500 mL of THF and the solution cooled to 0° C. A 3.0 M solution of phenylmagnesium bromide (310 mL, 920 mmol) in diethyl ether was added by cannula at this temperature over 5 min. During the addition some precipitate formed. The mixture was allowed to warm to room temperature. After 12 h, excess Grignard reagent was decomposed by the addition of 100 mL of concentrated ammonium chloride solution followed by 300 mL of water until all solids had dissolved. The organic layer was separated and the aqueous layer was extracted with 500 mL of diethyl ether. The organic layers were combined and dried over magnesium sulfate, filtered, concentrated, and the residue was treated with a mixture of 2000 mL of methanol, 150 mL of concentrated NH$_4$OH solution and 2000 mL of water. The organic layer was separated and the aqueous layer was extracted with 500 mL of chloroform. The organic layers were combined and washed with 600 mL of saturated sodium bicarbonate solution, dried over magnesium sulfate and concentrated in vacuo to give 101.6 g of crude nitroxide. The nitroxide was then purified by flash column chromatography (20:1 hexane: ethyl acetate) to afford 72.6 g (71% yield) of pure nitroxide as an orange oil, which crystallized at temperatures below 4° C. TLC (16:1 hexane:ethyl acetate, molybdenum stain): R$_f$=0.49; $^1$H NMR ((250 MHZ, CDCl$_3$) in the presence of pentafluorophenyl hydrazine): D 7.60–7.25 (m, 5H), 3.41 (d, 1H), 2.28 (m, 1H), 1.44 and 0.97 (s, 9H), 1.20 and 0.58 (d, 6H); $^{13}$C NMR ((63 MHZ, CDCl$_3$) in the presence of pentafluorophenyl hydrazine): D 154.26, 142.06, 141.20, 136.02, 129.50, 128.77, 128.43, 127.82, 127.25, 73.37, 71.31, 63.30, 59.10, 31.51, 31.23, 30.19, 26.85, 21.54, 20,55, 18.48

Part C: 2,2,5-Trimethyl-3-(1-phenylethoxy)-4-phenyl-3-azahexane

To a solution of styrene (4.48 g, 40 mmol) and 2.2,5-trimethyl-4-phenyl-3-azahexane-3-nitroxide (4.40 g, 20 mmol) in 1:1 toluene/ethanol (150 mL) was added [N,N'-bis-(3,5-di-t-butylsalicylidene)-1,2-cyclohexanediaminato] manganese(III) chloride (2.80 g, 4.0 mmol) followed by di-t-butyl peroxide (4.30 g, 30.0 mmol) and sodium borohydride (2.28 g, 60 mmol). The reaction mixture was then stirred at room temperature for 12 h, evaporated to dryness, partitioned between dichloromethane (150 mL) and water (200 mL), and the aqueous layer further extracted with dichloromethane (3×100 mL). The combined organic layers were then dried, evaporated to dryness, and the crude product purified by flash chromatography eluting with 1:9 hexane gradually increasing to 1:3 dichloromethane/hexane. The desired alkoxyamine was obtained as a colorless oil (4.03 g, 62%). The coupling product was determined to be a mixture of diastereomers as indicated by the integration of the methyl hydrogens at δ0.54 and 0.22 ppm.

Example 2

Preparation of 2,2,5-Trimethyl-3-(1-pyridinylethoxy)-4-phenyl-3-azahexane:

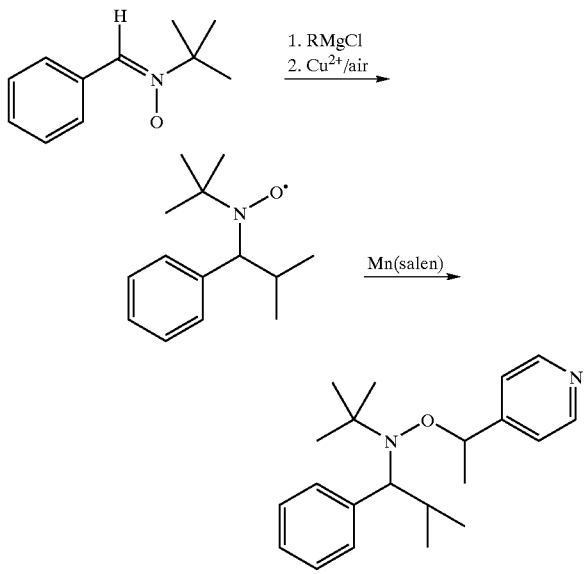

Scheme 2

N-tert-Butyl-α-phenylnitrone (355 mg, 5.0 mmol) was dissolved in 10 mL of anhydrous THF at room temperature under argon atmosphere and the solution cooled to 0° C. A 2 M solution of isoproprymagnesium chloride (2.0 mL, 4.0 mmol) in THF was added dropwise at this temperature with a syringe and the reaction mixture allowed to warm to room temperature with stirring overnight. Formation of the intermediate hydroxylamine and the corresponding nitroxide was observed by thin layer chromatography and GC/MS (M+.= 221 and 220, respectively). The reaction was quenched by addition of 10 mL of saturated aqueous NH$_4$Cl solution and the solvent was evaporated under reduced pressure. The residue was diluted in ether (20 mL) and the aqueous phase was extracted twice with 10 mL of ether. The combined organics were washed subsequently with 20 mL each of water and saturated aqueous NaCl solution, dried over MgSO$_4$, filtered and evaporated. Although the crude product mixture is already of sufficient purity for the oxidation step, the products were zisolated by flash chromatography on silica gel using EtOAc/hexanes (7:1) as an eluent to yield 378 g (85%) of a 1:1 mixture of the hydroxylamine and the corresponding nitroxide as an orange oil. Hydroxylamine: GC: R$_t$: 3.46 min.; MS: 221 (M+.), 178, 162, 146, 133, 122, 91, 57; $^1$H NMR (300 MHZ, CDCl$_3$): D=0.65 (d, J=6.0 Hz, 3H, CH(CH$_3$)$_2$), 1.00 (s, 9H, C(CH$_3$)$_3$), 1.21 (d, J=6.0 Hz, 3H, CH(CH$_3$)$_2$), 2.35 (br. m, 1H, CH(CH$_3$)$_2$), 3.46 (d, J=9,6 Hz, 1H, NCH), 4.05 (br. s, 1H, OH), 7.26–7.39 (br. m, 3H, m-/p-aryl-H), 7.42–7.52 (br. m, 2H, o-aryl-H) ppm.; $^{13}$C NMR (75 MHZ, CDCl$_3$): D=18.70, 19.78, 25.00, 29.58, 57.18, 69.39, 124.76, 125.85, 128.14, 140.02 ppm. Nitroxide: TLC (1:16 EtOAc/hexanes): R$_f$=0.49 (yellow spot in VIS); (1:4 EtOAc/hexanes): R$_f$=0.72 (yellow spot in VIS); GC: R$_t$: 3.502 min.; MS: 220 (M+.), 178, 162, 133, 122, 117, 91, 57,41; $^1$H NMR (300 MHZ, CDCl$_3$-pentafluorophenyl hydrazine):D=0.58 (d, J=6.0 Hz, 3H, CH(CH$_3$)$_2$), 0.97 (s, 9H, C(CH$_3$)$_3$), 1.12 (d, J=6.0 Hz, 3H, CH(CH$_3$)$_2$), 2.29 (br. m, 1H, CH(CH$_3$)$_2$), 3.40 (d, J=9.6 Hz, 1H, NCH), 3.6–4.1 (br. m, NH$_2$), 5.15 (br. m, NH), 7.15–7.31 (br. m, 3H, meta-/para-C—H), 7.38–7.22 (br. m, 2H, ortho-C—H) ppm.

The mixture of hydroxylamine and nitroxide (375 mg, approximately 1.7 mmol based on hydroxylamine) was dissolved in 10 mL of MeOH at room temperature. Approximately 2 mL of an aqueous solution of NH$_4$OH (approximately 28%) and a spatula tip of Cu(OAc)$_2$ were added. Air was bubbled through the vigorously stirred reaction mixture at room temperature. The reaction mixture turned from yellow to dark blue-green within approximately 10 min. and the reaction was carried on for another 30 min. Upon completion (as measured by t.l.c., GC/MS), the organic solvent was removed under reduced pressure and the residue was diluted with 50 mL of dichloromethane. The aqueous phase was extracted twice with 20 mL of dichloromethane and the combined organics were subsequently washed with 50 mL each of a 5% aqueous KHSO$_4$ solution, a saturated aqueous NaHCO$_3$ solution, water and a saturated aqueous NaCl solution. Drying over MgSO$_4$, filtration, and evaporation followed by purification by column chromatography on silica gel using EtOAc/hexanes (1:19) as eluent (collection of the yellow fraction) yielded 332 mg (89%) of pure 2,2,5-trimethyl-4-phenyl-3-azahexane-3-nitroxide as a deep orange viscous oil which solidified in the refrigerator (−20° C.). Both GC/MS and $^1$H NMR spectroscopy in the presence of 2 eq. of pentafluorophenyl hydrazine showed homogeneity of the product obtained.

A 100 mL round-bottomed flask equipped with a stirring bar and a PE stopper penetrated by a long stainless steel needle (air inlet) and two short needles (air outlet) was charged with 2,2,5-trimethyl-4-phenyl-3-azahexane-3-nitroxide (661 mg, 3.0 mmol). EtOH/toluene (1:1) (30 mL) and Jacobsen's Mn-salen complex (286 mg, 0.45 mmol) were added. Subsequently, 473 mg (4.5 mmol, 485 μL) of 4-vinylpyridine were added via syringe followed by 227 mg (6.0 mmol) of NaBH$_4$. Air was bubbled through the (dark brown, cloudy) reaction mixture for approximately 12 h at room temperature. After filtration over a short plug of silica gel, EtOH and toluene were removed under reduced pressure and the residue was dissolved in 25 mL of EtOAc/hexanes (1:1). The filter residue was washed with EtOAc/hexanes (1:1). The combined organics were washed with water and saturated aqueous NaCl solution, dried (MgSO$_4$), filtered, and evaporated under reduced pressure. The alkoxyamine was eluted from the residue by means of MPLC with EtOAc/hexanes (1:4) to yield 747 mg (76%) of a 1:1 mixture of diastereomers of 2,2,5-Trimethyl-3-(1-pyridinylethoxy)-4-phenyl-3-azahexane as a dark yellow viscous oil. TLC (1:4 EtOAc/hexanes): R$_f$=0.26; GC: R$_t$: decomposition; $^1$H NMR (300 MHZ, CDCl$_3$, both diastereoisomers): D=0.25 (d, J=6.6 Hz, 3H, CH(CH$_3$)$_2$), 0.53 (d, J=6.6 Hz, 3H, CH(CH$_3$)$_2$), 0.78 (s, 9H, C(CH$_3$)$_3$), 0.93 (d, J=6.3 Hz, 3H, CH(CH$_3$)$_2$), 1.02 (s, 9H, C(CH$_3$)$_3$), 1.24 (d, J=7.2 Hz, 3H, CH(CH$_3$)$_2$), 1.38–1.50 (br. m, superimposed, 1H, CH(CH$_3$)$_2$), 1.52 (d, J=6.6 Hz, 3H, COHCH$_3$), 1.59 (d, J=6.6 Hz, 3H, COHCH$_3$), 2.28 (br. m, 1H, CH(CH$_3$)$_2$), 3.33 (d, J=10.8 Hz: 1H, CHN), 3.41 (d, J=10.8 Hz, 1H, CHN), 4.81–4.96 (2q, superimposed, J=6.6 Hz, 2H, COHCH$_3$), 7.10–7.29 (br. m, 10H, Ph), 7.30–7.48 (br. m., 4H, pyridyl-H), 8.44–8.65 (br. m., 4H, pyridyl-H) ppm.; $^{13}$C NMR (75 MHZ, CDCl$_3$, both diastereoisomers): D=15.20, 20.99, 21.72, 21.84, 22.57, 22.93, 24.34, 28.11, 28.31, 31.51, 31.88, 31.98, 60.52, 60.59, 65.76, 72.00, 72.16, 81.22, 82.40, 121.05, 121.74, 126.34, 126.44, 127.29, 127.40, 130.60, 130.78, 141.81, 142.00, 149.67, 153.41, 154.24 ppm.

Example 3

2,2,5-trimethyl-3-(1-phenylethoxy)-4-(3-pyridyl)-3-azahexane

Scheme 3

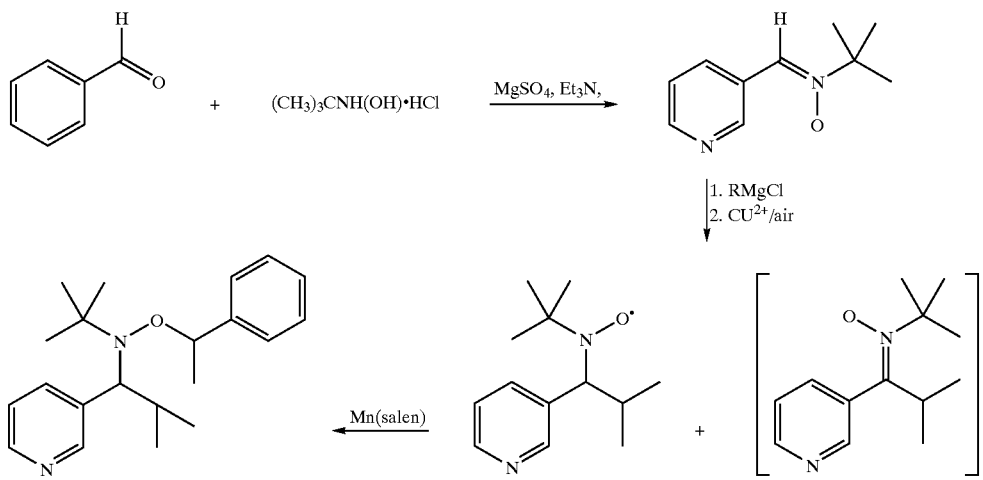

Part A: Preparation of N-tert-Butyl-α-(3-pyridyl) nitrone

To a mixture of N-tert-butylhydroxylamine hydrochloride (2.512 g, 20.0 mmo 1), pyridine-3 -carboxaldehyde (2.144 g, 20.0 mmol), and MgSO4 (2.889 g, 22.0 mmol) was added 100 mL of anhydrous toluene followed by 2.024 g (20.0 mmol/2.79 mL) of Et3N. The reaction mixture was heated to 100–110° C. under argon atmosphere, and the reaction course was followed by t.l.c. and GC/MS. After 3–5 hours, the reaction was cooled to room temperature, Mg SO4 was filtered off, and the solvent was evaporated under reduced pressure to yield a dark yellow-green mixture of product and Et3N.HCl. The crystals were dissolved in EtOAc and the solution was subsequently washed with saturated aqueous NaHCO3, water and saturated aqueous NaCl, dried (MgSO4 or Na2SO4, ca. 30 min), filtered, and evaporated under reduced pressure. The crude product was purified by passing through a short plug of silica gel (1:1 EtOAc/hexanes) to yield after evaporation 3.00 g (84%) of a pale yellow solid. TLC (1:9 EtOAc/hexanes): $R_f$=0.61; GC: $R_t$: 3.92 min; MS: 178 (M+.), 147, 122 (b.p.), 106, 79, 57; $^1$H NMR (300 MHZ, CDCl$_3$): D=1.54 (s, 9H, C(CH$_3$)$_3$), 7.31 (dd, J=8.1,4.8 Hz, 1H, C(5)-H), 7.56 (s, 1H, HC=N), 8.53 (dd, J=4.8,1.8 Hz, 1H, C(6)-H), 8.93 (d, J=1.8 Hz, 1H, C(2)-H), 9.06 (dt, J=8.4,1.8 Hz, 1H, C(4)-H) ppm; $^{13}$C NMR (75 MHZ, CDCl$_3$): D=28.24 71.43, 123.40, 126.91, 127.49, 134.57, 150.09, 150.20 ppm.

Part B: Preparation of 2,2,5-trimethyl-3-(1-phenylethoxy))-4-(3-pyridyl)-3-azahexane N-tert-Butyl-α-(3-pyridyl) nitrone (891 mg, 5.0 mmol) was dissolved in 50 mL of anhydrous THF at room temperature. The yellowish solution was cooled to 0° C. and isoproprymagnesium chloride (2 M in THF, 5.0 mL, 10.0 mmol) was added dropwise at this temperature with a syringe. The reaction mixture was stirred overnight with warming to room temperature (bright yellow to brownisch clear solution). GC/MS showed formation of the intermediate hydroxylamine (GC: $R_t$: 3.803 min.; MS: 222 (M+.), 179, 163, 147, 134, 123, 107, 92, 78, 57, 41) accompanied by some nitroxide (GC: $R_t$: 3.752 min.; MS: 221 (M+.), 204, 179, 163, 147, 134, 120 (b.p.), 107, 92, 78, 57, 41). The solvent was evaporated under reduced pressure and the residues were redissolved in 50 mL of MeOH. 5.0 mL of 28% aqueous NH$_4$OH was added (with some precipitation of Mg(OH)$_2$) and a spatula tip of Cu(OAc)$_2$ was added. Air was bubbled through the well stirred yellowish reaction mixture for 2–3 hours at room temperature until the reaction mixture turned significantly green-blue. MeOH and water were removed under reduced pressure and the remaining crude product was redissolved in dichloromethane/water. The aqueous phase was extracted twice with dichloromethane and the combined organic phase was washed with water and saturated aqueous NaCl. Drying (MgSO4, 30 min), filtration, and evaporation yielded the crude nitroxide. Both, t.l.c. and GC/MS showed the formation of the nitroxide (GC: $R_t$: 3.752 min.; MS: 221 (M+.), 204, 179, 163, 147, 134, 120 (b.p.), 107, 92, 78, 57, 41) with some impurity of the nitrone (GC: $R_t$: 4.718 min.; MS: 220 (M+., due to overoxidation), 189, 164, 147 (b.p.), 130, 120,:106, 92, 80, 57, 41) in a ratio of ca. 10:1.

The crude reaction mixture was dissolved in 50 mL EtOH/toluene (1:1) and Jacobsen's Mn-salen complex (476 mg, 0.75 mmol) was added. Subsequently, styrene (781 mg, 7.5 mmol, 860 μl) and NaBH4 (374 mg, 10.0 mmol) were added and air was bubbled through the dark brown, cloudy reaction mixture 12 hours at room temperature. After filtration over a short plug of silica gel, EtOH and toluene were removed under reduced pressure and the residue was dissolved in 25 mL of 1:1 EtOAc/hexanes. The filter residue was washed with 1:1 EtOAc/hexanes and the organics were combined. The organics were washed with water and saturated aqueous NaCl, dried (MgSO4), filtrated, and evaporated under reduced pressure. The alkoxyamine was eluted from the residue by means of MPLC with EtOAc/hexanes (1:4) to yield 1.169 g (72%) of a slightly yellow viscous oil. Purity and product homogeneity were determined by t.l.c. and 1H- and 13C NMR spectroscopy. 1H- and 13C NMR spectroscopy showed that the product was a mixture of diastereoisomers in a ratio of ca. 1:1. TLC (1:4 EtOAc/hexanes) $R_f$=0.31; GC: $R_t$: decomposition; $^1$H NMR (300 MHZ, CDCl$_3$, both diastereoisomers):D 0.19 (d, J=6.6 Hz, 3H, CH(CH$_3$)$_2$), 0.54 (d, J=6.6 Hz, 3H, CH(CH$_3$)$_2$), 0.77 (s, 9H, C(CH$_3$)$_3$), 0.91 (d, J=6.3 Hz, 3H, CH(CH$_3$)$_2$), 1.03 (s, 9H, C(CH$_3$)$_3$), 1.19–1.34 (br. m. superimposed, 1H, CH(CH$_3$)$_2$), 1.31 (d, J=6.6 Hz, 3H, CH(CH$_3$)$_2$), 1.53 (d, J=6.6 Hz, 3H, COHCH$_3$), 1.62 (d, J=6.6 Hz, 3H, COH (CH$_3$), 2.22–2.41 (m, 1H, CH(CH$_3$)$_2$), 3.31 (d, J=10.8 Hz, 1H, NCH), 3.31 (d, J=10.8 Hz, 1H, NCH), 3.45 (d, J=11.1 Hz, 1H, NCH), 4.83–4.95 (2q, superimposed, 2H, COH (CH$_3$), 7.15–7.32 (m, 5H, Ph), 7.55–7.66 (br. m, 1H, pyridyl-H), 7.82–7.88 (br. m, 1H, pyridyl-H), 8.34–8.62 (v. br. m., 2H, pyridyl-H) ppm; $^{13}$C NMR (75 MHZ, CDCl$_3$): D=20.82, 20.98, 21.74, 21.98, 22.70, 24.52, 25.22, 28.27, 28.43, 31.44, 31.98, 60.50, 60.67, 69.53, 69.71, 70.18, 83.08, 83.59, 12.51, 122.69, 125.36, 126.08, 126.77, 127.03, 127.30, 127.54, 128.11, 128.14, 128.40, 128.99, 137.48, 137.70, 138.15, 138.20, 144.45, 145.17, 146.05, 147.48, 147.70, 151.69 ppm.

Example 4

Reaction of 5,5-Dimethyl-Δ$^1$-pyrroline N-oxide with AIBN

Scheme 4

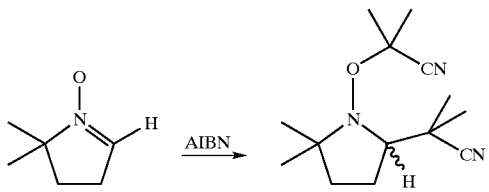

A 25 mL oven dried Schlenk flask equipped with stirring bar and rubber septum was charged under argon with 620 mg (5.9 mmol) of 5,5-dimethyl-Δ$^1$-pyrroline N-oxide (Aldrich, Milwaukee, Wis.) and 1.94 g (11.8 mmol) of azobisisobutyrodinitrile (AIBN). 2 mL of deoxygenated xylene were added and the stirred reaction mixture was heated under argon to 105–110° C. until the evolution of nitrogen ceased. Xylene was evaporated in vacuo and 1 mL of petroleum ether was added to the reaction mixture to yield an orange solution. 5 mL of MeOH were added under vigorous stirring and after phase separation and removal of the supernatant, the methanolic layer was partially concentrated and placed in a refrigerator at approximately –20° C. causing colorless crystals to form. Excess MeOH was removed and the residue was dissolved in approximately 2 mL of MeOH under gentle heating. The solution was again cooled to approximately –20° C. and, after collection, the crystals were dried in vacuo to yield 401 mg (27%) of the desired compound. TLC (1:9 EtOAc/hexanes): R$_f$=0.60; $^1$H NMR (300 MHZ, CDCl$_3$): D 1.22 (s, 3H, CH$_3$), 1.34 (s, 3H, CH$_3$), 1.37 (s, 3H, CH$_3$), 1.43 (s, 3H, CH$_3$), 1.4–1.7 (m, superimposed, 3H, CH$_2$CHHCH), 1.74 (s, 3H, CH$_3$), 1.76 (s, 3H, CH$_3$), 1.95 (dq, J=12.0 9.6 Hz, 1H, CH$_2$CHHCH), 3.30 (dd, J=10.1, 5.9 Hz, 1H, CH$_2$CHHCH) ppm; $^{13}$C NMR (75 MHZ, CDCl$_3$): D=20.85, 21.60, 22.03, 24.96, 26.09, 28.44, 34.90, 37.31, 39.34, 66.37, 72.33, 73.86, 121.39, 126.01 ppm.

Example 5

Comparison: TEMPO in Emulsion Polymerization

Twelve (12) separate emulsion polymerization reactions were conducted with three different initiators, all at 90° C. for 15 h (a total of 36 experiments). Each polymerization was set up with a total volume 0.7 mL, with 20 weight % styrene (monomer). The amount of surfactant (sodium alpha ($C_{14}$–$C_{16}$) olefin sulfonate—sold by Rhodia as Rhodacal A-246/L) added was 1 weight % to monomer, and the amount of initiator added was 0.001 mole equivalents to monomer. The initiators that were used were water soluble and were (1) potassium persulfate, (2) tert-butylhydroperoxide (TBHP) and (3) 2,2-azobis(N,N'-dimethyleneisobutyramidine) dihydrochloride (sold by E. I. du Pont de Nemours and Company under the trademark VAZO® 044). For each initiator the series of 12 polymerizations differed in the amount of control agent added, with the first well getting no control agent and the last well getting 3.3 mole equivalents of control agent, with even steps of 0.3 mole equivalents (the control agent used was 2,2,6,6-tetramethyl-1-piperidinoxyl radical—"TEMPO"). After the predetermined heating and agitation time and temperature the polymerization mixtures were worked up and characterized using the standard procedure outlined for polymerization experiments at the beginning of the Example section.

Figure 1B:
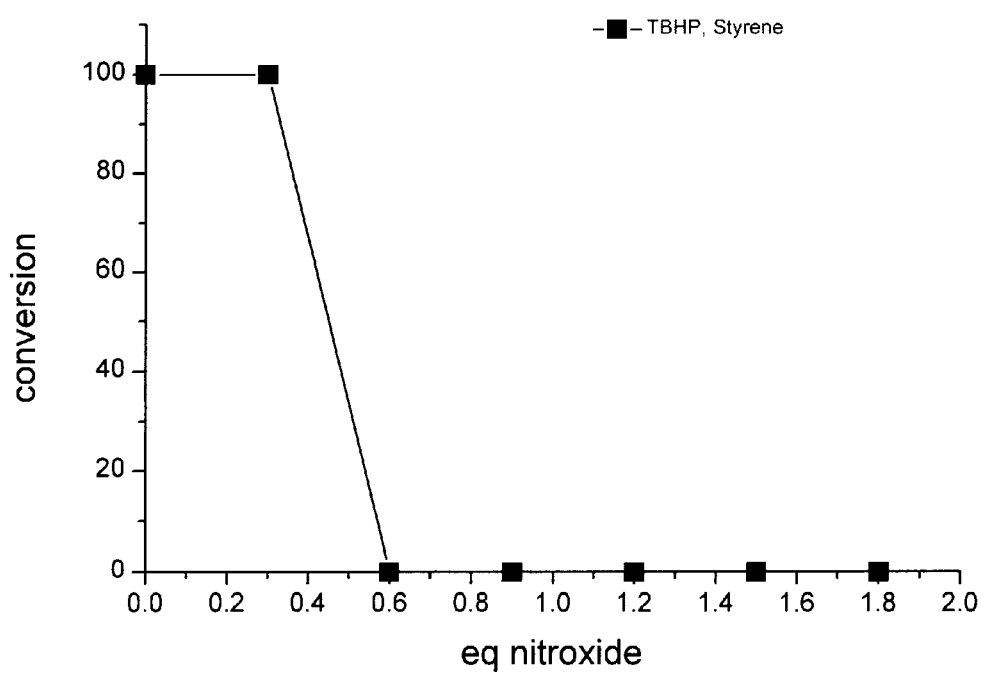

FIGS. 1A and 1B plot the results of the above experiments for TBHP and demonstrate that with styrene as the monomer and TEMPO as the control agent the polymerization goes from an uncontrolled radical polymerization to complete inhibition over a very small change in TEMPO concentration. Upon adding 0.3 equivalents of TEMPO to the free radical emulsion polymerization the weight average molecular weight (M$_w$) and the conversions remain unchanged from the polymerization containing no TEMPO. However, upon addition of 0.6 equivalents or more monomer consumption is completely stopped.

Example 6

A-Hydrido-Nitroxide Control Agent in Emulsion Polymerization

Thirty six, stable free radical polymerization reactions were carried out under aqueous emulsion conditions. Each polymerization was set up with a total volume 0.7 mL, with 20 weight % styrene (monomer). The amount of surfactant (sodium alpha ($C_{14}$–$C_{16}$) olefin sulfonate—sold by Rhodia as Rhodacal A-246/L) added was 1 weight % to monomer, and the amount of initiator added was 0.001 mole equivalents to monomer. The initiators that were used were water soluble and were (1) potassium persulfate, (2) tert-butylhydroperoxide (TBHP) and (3) 2,2-azobis(N,N'-dimethyleneisobutyramidine) dihydrochloride (sold by E. I. du Pont de Nemours and Company under the trademark VAZO® 044). For each initiator the series of 12 polymerizations differed in the amount of control agent added, with the first well getting no control agent and the last well getting 3.3 mole equivalents of control agent, with even steps of 0.3 mole equivalents (the control agent used was 2,2,5-trimethyl-4-phenyl-3-azahexane-3—nitroxide - "A-hydrido-nitroxide"). After the predetermined heating and agitation time and temperature (90° C. for 15 h) the emulsions were worked up and characterized using the standard procedure outlined for polymerization experiments at the beginning of the Example section. Polymer was produced in all of the emulsion polymerization mixtures.

Figure 2A:
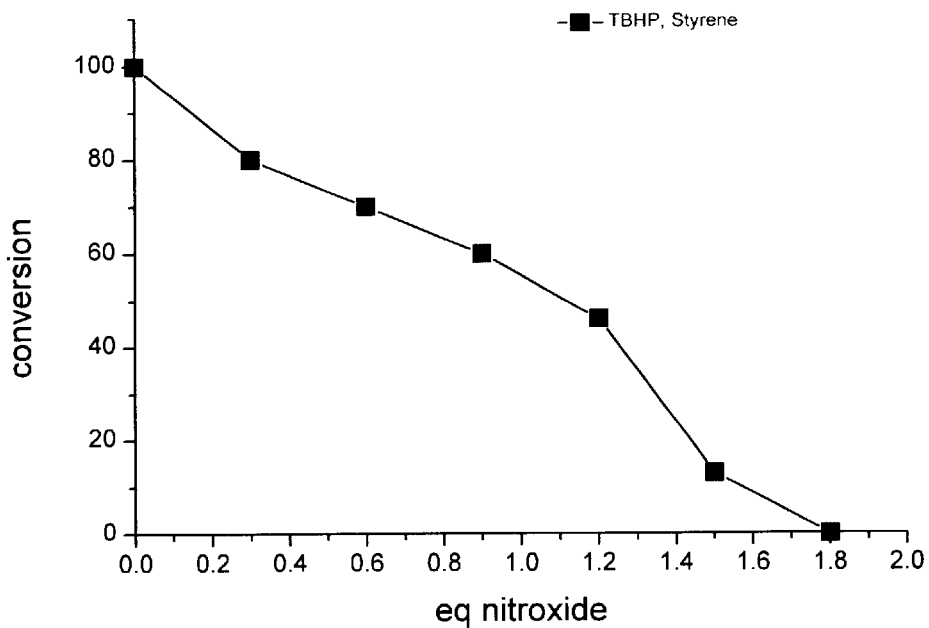
FIGS. 2A and 2B are graphs showing molecular weight and conversion as a function of increasing concentration of an α-hydrido nitroxide control agent for the heterogeneous polymerization of styrene.
Figure 2B:
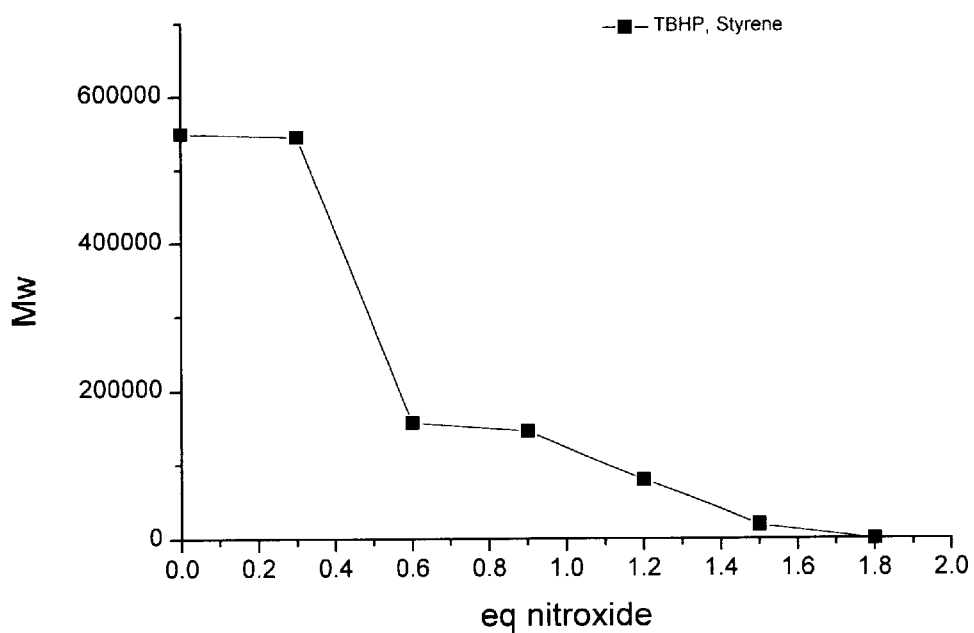

FIGS. 2A and 2B graphically display the results for the polymerizations where TBHP is used as the initiator. FIG. 2A shows a graph of conversion versus equivalents of nitroxide and FIG. 2B shows a graph of molecular weight versus equivalents of nitroxide. Upon adding from 0.3 equivalents (eq) to 1.5 eq of 2,2,5-trimethyl-4-phenyl-3-azahexane-3-nitroxide (A-hydrido-nitroxide) to the free radical emulsion polymerization the weight average molecular weight (M$_w$) and the conversions are reduced in an almost linear fashion. Table 3, below provides selected molecular weight and conversion data.

TABLE 3

| Initiator | A-hydrido-nitroxide to initiator ratio | $M_w$ | Conversion |
|---|---|---|---|
| $K_2S_2O_8$ | 0:1 | 749,265 | 99 |
| $K_2S_2O_8$ | 0.3:1 | 527,763 | 98 |
| $K_2S_2O_8$ | 0.6:1 | 326,648 | 69 |
| $K_2S_2O_8$ | 0.9:1 | 146,769 | 26 |
| $K_2S_2O_8$ | 1.2:1 | 102,554 | 10 |
| TBHP | 0:1 | 544,236 | 97 |
| TBHP | 0.3:1 | 541,576 | 80 |
| TBHP | 0.6:1 | 155,490 | 44 |
| TBHP | 0.9:1 | 143,790 | 60 |
| TBHP | 1.2:1 | 77,163 | 46 |
| TBHP | 1.5:1 | 19,000 | 13 |
| VAZO ® 044 | 0:1 | 570,640 | 95 |
| VAZO ® 044 | 0.3:1 | 252,908 | 44 |
| VAZO ® 044 | 0.6:1 | 111,664 | 26 |

Example 7

Sixty four stable free radical polymerization reactions were carried out under aqueous emulsion conditions. Each polymerization was set up with a total volume 0.7 mL, with 20 weight % styrene (monomer). The amount of surfactant (sodium alpha ($C_{14}$–$C_{16}$) olefin sulfonate—sold by Rhodia as Rhodacal A-246/L) added was 1 weight % to monomer, and four different amounts of initiator were added: 0.001, 0.002, 0.003 and 0.004 mole equivalents to monomer. Two initiators different that were used were water-soluble and were (1) potassium persulfate, (2) tert-butylhydroperoxide (TBHP). For each initiator the series of seven polymerizations differed in the amount of control agent added, with the first well getting 0.6 mole equivalents control agent and the last well getting 1.2 mole equivalents of control agent, with even steps of 0.1 mole equivalents (the control agent used was 2,2,5-trimethyl-4-phenyl-3-azahexane-3-nitroxide—"A-hydrido-nitroxide"). In addition a polymerization reaction without control agent was conducted for each initiator type and amount. Four chemically identical copies were made, agitated and heated at 90° C. for 3, 7, 15 and 30 h respectively (thus a total of 256 different polymerizations were actually carried out). After the predetermined heating and agitation time the emulsions were worked up and characterized using the standard procedure outlined for polymerization experiments at the beginning of the Example section. The polymers obtained from these experiments showed a wide range of molecular weights.

Figure 3A:
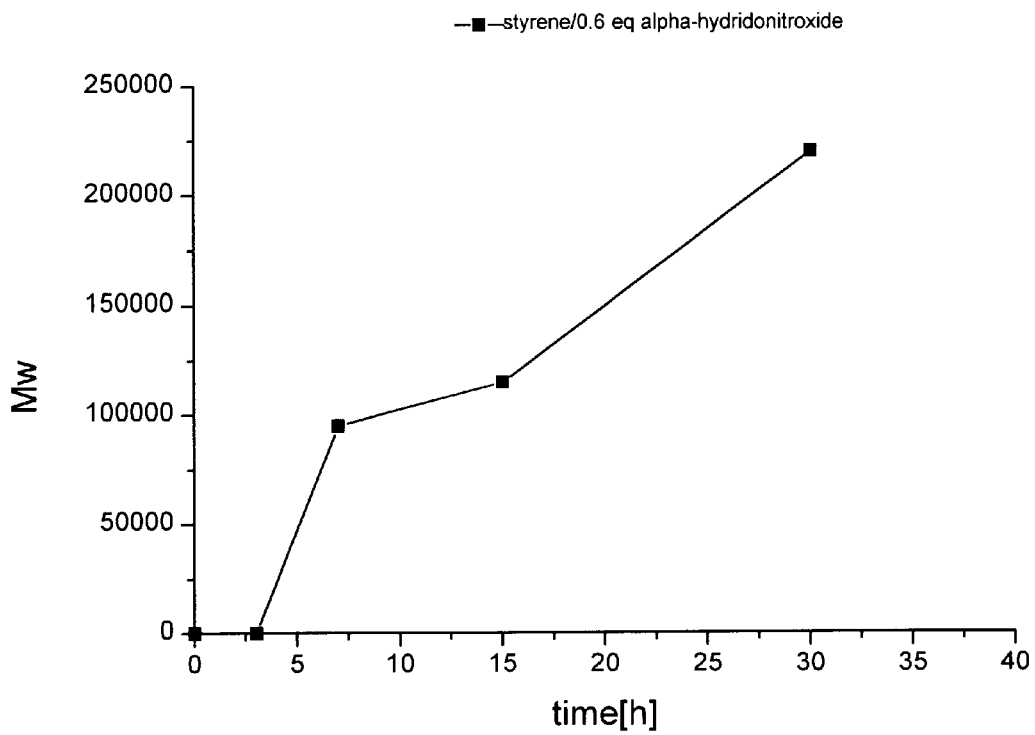
FIGS. 3A–3E are graphs demonstrating the living kinetics achieved with this invention as well as control of molecular weight and conversion based concentration of an α-hydrido nitroxide control agent.
Figure 3B:
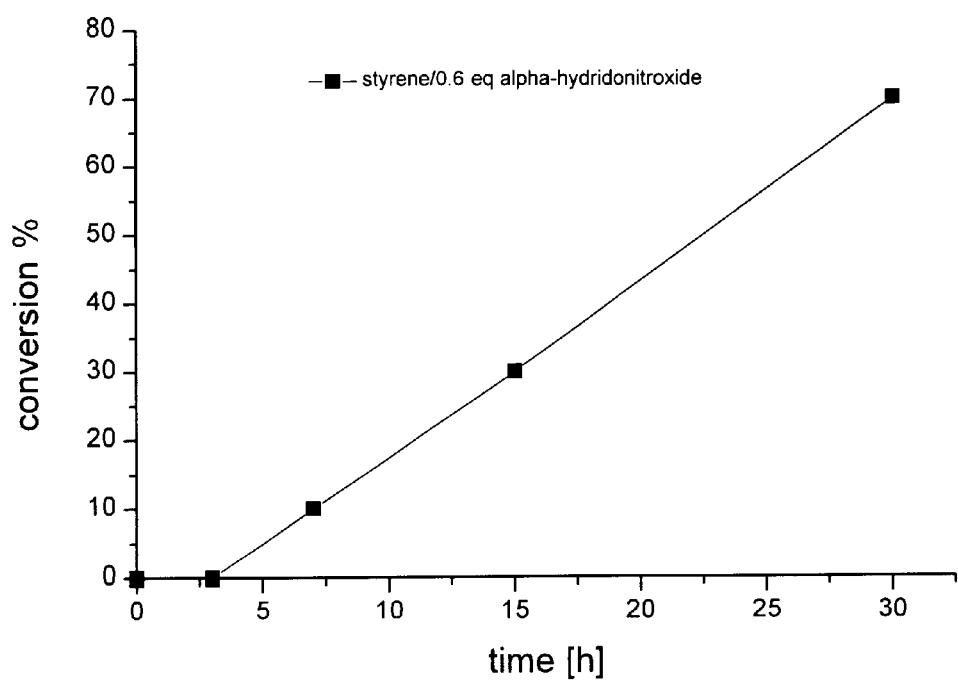
Figure 3C:
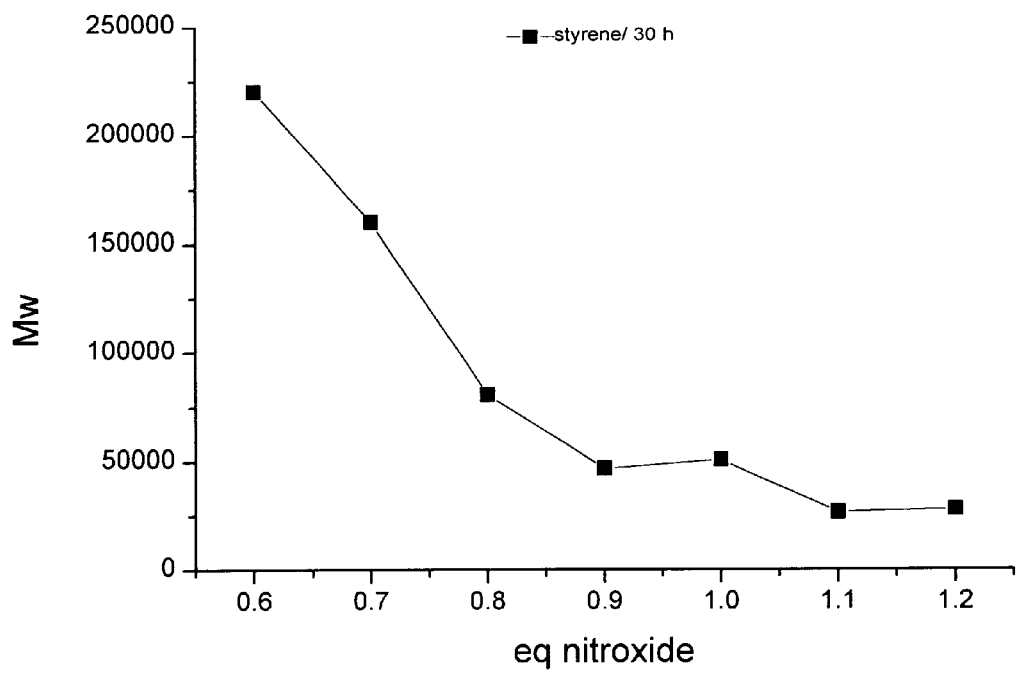
Figure 3D:
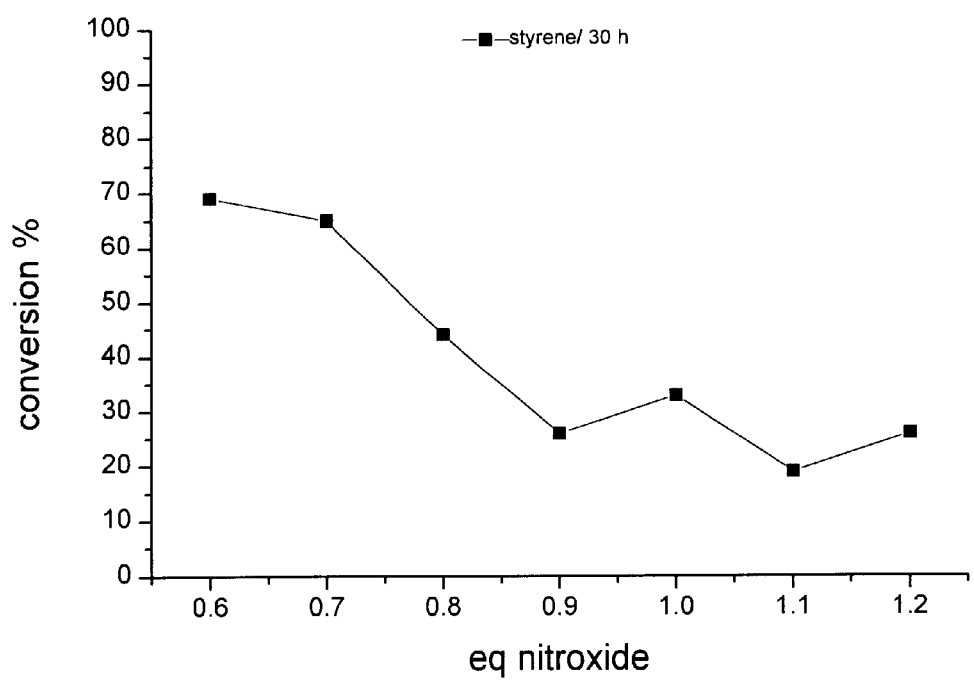
Figure 3E:
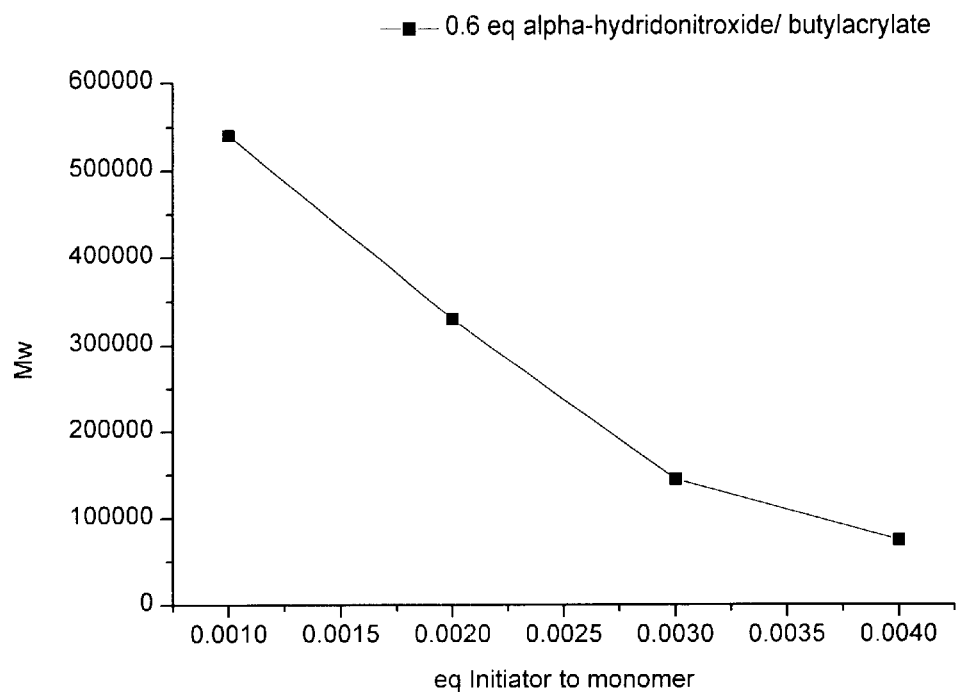

FIGS. 4A–E graphically display selected results from these polymerizations. FIG. 3A graphs weight average molecular weight versus reaction time (for 0.6 equivalents of A-hydrido-nitroxide for the initiator TBHP at an initiator to monomer ratio of 0.001 and at 0.6 equivalents of A-hydrido-nitroxide to initiator). FIG. 3B graphs conversion versus reaction time (for 0.6 equivalents of A-hydrido-nitroxide for the initiator TBHP at an initiator to monomer ratio of 0.001 and at 0.6 equivalents of A-hydrido-nitroxide to initiator). FIG. 3C graphs weight average molecular weight versus equivalents of A-hydrido-nitroxide (for the initiator TBHP at a 30 hour polymerization time and at an initiator to monomer ratio of 0.001). FIG. 3D graphs conversion versus equivalents of A-hydrido-nitroxide (for the initiator TBHP at a 30 hour polymerization time and at an initiator to monomer ratio of 0.001). FIG. 3E graphs weight average molecular weight versus the ratio of initiator to monomer (for the initiator TBHP at 0.6 equivalents of A-hydrido-nitroxide to initiator at a 30 hour polymerization time). As was previously shown in example 3, by increasing the ratio of A-hydrido-nitroxide to the free radical initiator from 0.6 eq to 1.2 eq the weight average molecular weight ($M_w$) and the conversions are decreased in a linear fashion. These graphs also show several trends that are known to be associated with living polymerizations. There is a linear relationship between molecular weight and the reaction time, as well as between the conversion and the reaction time. In addition, upon increasing the amount of initiator (while keeping the nitroxide to initiator ratio constant) there is a linear decrease in molecular weight.

Example 8
Block Styrene/n-Butylacrylate Polymers

Sixteen stable free radical polymerization reactions were carried out under aqueous emulsion conditions. Each polymerization was set up with a total volume 0.7 mL, with 10 weight % styrene (monomer). The amount of surfactant (sodium alpha ($C_{14}$–$C_{16}$) olefin sulfonate—sold by Rhodia as Rhodacal A-246/L) added was 1 weight % to monomer, and two different amounts of initiator were added: 0.001 and 0.002 mole equivalents to monomer. The initiator that was used was water soluble and was tert-butylhydroperoxide (TBHP). For each initiator concentration the series of seven polymerizations differed in the amount of control agent added, with the first well getting 0.6 mole equivalents control agent and the last well getting 1.2 mole equivalents of control agent, with even steps of 0.1 mole equivalents (the control agent used was 2,2,5-trimethyl-4-phenyl-3-azahexane-3-nitroxide—"A-hydrido-nitroxide"). In addition a polymerization reaction without control agent was conducted for each amount of initiator. After the predetermined heating and agitation time of 90° C. and 30 h the reactor vessels were opened and a small aliquot was taken from each vessel for analysis. Subsequently, an mass of n-butylacrylate equal to the amount of styrene previously added (10 wt %) was dispensed to each vessel. The vessels were then resealed and heated at 90° C. and mixed for an additional 30 hours. Subsequently the emulsions were worked up and characterized using the standard procedure outlined for polymerization experiments at the beginning of the Example section.

Figure 4:
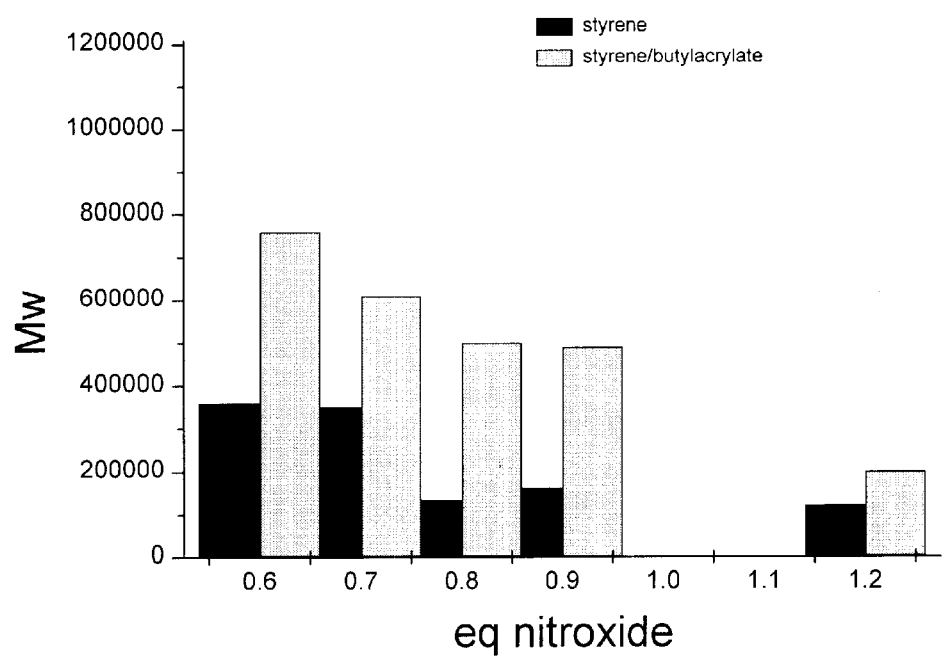
FIG. 4 is a bar graph showing molecular weight as a function of the concentration of an α-hydrido nitroxide control agent for both styrene polymers and styrene/butylacrylate copolymers.

FIG. 4 is a bar graph of the molecular weight versus the amounts of control agent for both steps of the block copolymerization (styrene polymerization—block A, and butylacrylate polymerizations—block B). Upon polymerizing the second monomer, there was a clear increase of the molecular weights as compared to the molecular weights obtained after polymerization of just the first monomer, suggesting block copolymer formation. In addition, the overall molecular weights (after polymerization of the second monomer) still depended on the ratio of 2,2,5-trimethyl-4-phenyl-3-azahexane-3-nitroxide (A-hydrido-nitroxide control agent) to initiator which suggests that the polymerization had not lost its living character.

Example 9
Block n-Butylmethacrylate/Styrene Polymers

Twenty four stable free radical polymerization reactions were carried out under aqueous emulsion conditions. Each polymerization was set up with a total volume of 0.7 mL, with 10 weight % n-butylmethacrylate (monomer), 1 wt % to monomer of surfactant (sodium alpha ($C_{14}$–$C_{16}$) olefin sulfonate—sold by Rhodia as Rhodacal A-246/L), and three different amounts of initiator—0.001, 0.002, and 0.003 mole equivalents to monomer. The initiator that was used was water soluble and was tert-butylhydroperoxide (TBHP). For each initiator concentration the series of seven polymerizations differed in the amount of control agent—2,2,5-trimethyl-4-phenyl-3-azahexane-3-nitroxide ("A-hydrido-nitroxide") added, with the first well getting 0.6 mole equivalents of control agent and the last well getting 1.2 mole equivalents of control agent, with even steps of 0.1 mole equivalents. In addition, a polymerization reaction without control agent was conducted for each initiator amount. After the predetermined heating and agitation time of 90° C. and 30 hours the reactor vessels were opened and a small aliquot was taken from each vessel for analysis.

Subsequently, 10 wt % of a second monomer, styrene, was dispensed into each vessel. The vessels were then resealed and heated at 90° C. and mixed for an additional 30 hours. The emulsions were worked up and characterized using the standard procedure outlined for polymerization experiments at the beginning of the Example section.

Figure 5:
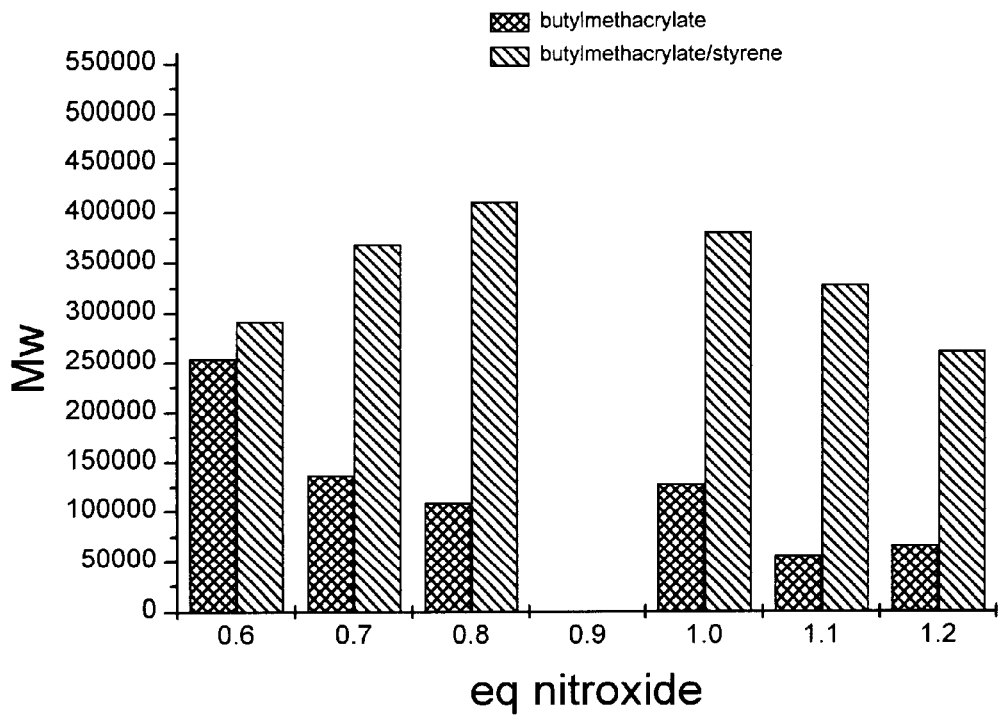
FIG. 5 is a bar graph showing molecular weight as a function of the concentration of an α-hydrido nitroxide control agent for both butylmethacrylate polymers and styrene/butylmethacrylate copolymers.

FIG. 5 is a bar graph of the molecular weight versus the amounts of control agent for both steps of the block copolymerization (n-butylmethacrylate polymerization—block A, and styrene polymerizations—block B). Upon polymerizing the second monomer, there was a clear increase of the molecular weights as compared to the molecular weights obtained after polymerization of just the first monomer, suggesting block copolymer formation. Table 4 below provides selected weight average molecular weights for the n-butylmethacrylate polymer and the block copolymer.

TABLE 4

| Initiator Concentration | A-hydrido-nitroxide to initiator ratio | $M_w$ of n-butyl-methacrylate | $M_w$ of block copolymer |
| --- | --- | --- | --- |
| 0.001 | 0.6:1 | 254,350 | 291,750 |
| 0.001 | 0.7:1 | 137,370 | 369,130 |
| 0.001 | 0.8:1 | 108,300 | 410,940 |
| 0.001 | 1:1 | 128,870 | 381,270 |
| 0.001 | 1.1:1 | 56,076 | 326,360 |
| 0.001 | 1.2:1 | 66,222 | 261,820 |
| 0.002 | 0.6:1 | 87,128 | 215,110 |
| 0.002 | 0.7:1 | 66,036 | 218,450 |
| 0.002 | 0.8:1 | 59,736 | 238,230 |
| 0.002 | 0.9:1 | 90,003 | 218,400 |
| 0.002 | 1:1 | 48,078 | 219,390 |
| 0.002 | 1.1:1 | 26,565 | 203,920 |
| 0.002 | 1.2:1 | 33,049 | 308,390 |
| 0.002 | 0:1 | 2,621,800 | — |
| 0.003 | 0.6:1 | 59,554 | 182,110 |
| 0.003 | 0.7:1 | 48,574 | 153,210 |
| 0.003 | 0.8:1 | 69,326 | 241,970 |
| 0.003 | 0.9:1 | 54,997 | 125,490 |
| 0.003 | 1:1 | 49,282 | 192,670 |
| 0.003 | 1.1:1 | 32,574 | Er |
| 0.003 | 1.2:1 | 20,079 | Er |
| 0.003 | 0:1 | 2,768,000 | — |

In Table 3, "Er" indicates an error in the testing and "—" indicates no data was taken.

Example 10
Stepwise Addition of Monomers

Sixteen stable free radical polymerization reactions were carried out under aqueous emulsion conditions. Each polymerization was designed to have the following final conditions for the growth of a first block: total volume of 0.7 mL, with 10 weight % of monomer, one weight % to monomer of surfactant (sodium alpha ($C_{14}$–$C_{16}$) olefin sulfonate—sold by Rhodia as Rhodacal A-246/L), and two different amounts of initiator—0.001, 0.002 mole equivalents to monomer. The initiator used was an adduct of the initiator/control agent (the organic soluble 2,2,5-trimethyl-3-(1-phenylethoxy)-4-phenyl-3-azahexane) (eight identical reactions were run at each initiator to monomer ratio). This compound predetermines the control agent to initiator ratio to equal one.

A first homopolymer block was assembled in two stages, with all the components except monomer being added in the first step. In the first step 2.5 wt % of styrene (25% of the total first monomer) was added to each reaction vessel, and the plate was sealed and heated at 90° C. for 6 hours. The reactor vessels were allowed to cool, were opened and the remaining 7.51 wt % of styrene (75% of the first monomer) was added to each reaction vessel. The vessels were then resealed and heated at 90° C. for an additional 30 hours. The reactor vessels were cooled to room temperature and opened and a small aliquot was taken. from each vessel for analysis.

Subsequently, 10 wt % of a second monomer, n-butylacrylate, was dispensed into each vessel. The vessels were then resealed and heated at 90° C. and mixed for an additional 30 hours. The emulsions were worked up and characterized using the standard procedure outlined for polymerization experiments at the beginning of the Example section.

Figure 6:
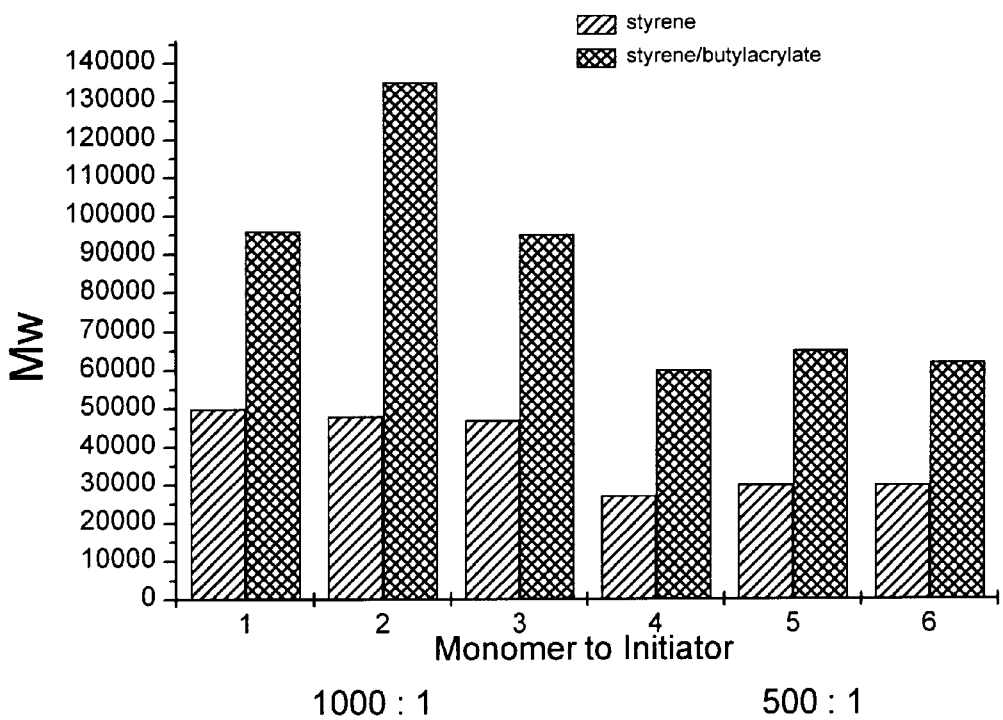
FIG. 6 is a bar graph showing molecular weight as a function of the ratio of monomer to initiator for both styrene polymers and styrene/butylacrylate copolymers.

FIG. 6 is a bar graph plotting monomer to initiator ratio versus weight average molecular weight for the two different initiator concentrations. Visual inspection of the reaction mixtures after the first step of the first block shows formation of stable emulsions as well as the absence of both monomer pool and precipitated solids (which are present when polymerization occurs in the monomer pool). This result demonstrated that the two step procedure described above allowed for use of organic soluble initiators in emulsion polymerizations. With dispensing the majority of the first monomer after 6 hours and a second monomer after 30 hours, we observe increases of molecular weight in both cases, suggesting chain extension and block copolymerization (characteristics of a living type polymerization), respectively.

Example 11
Initiator/control Agent Adduct in Emulsion Polymerization

Fifty six stable free radical polymerization reactions were carried out under aqueous emulsion conditions. Each polymerization was set up to have the following final conditions for the growth of a first block: total volume 0.7 mL, with 10 or 5 weight % styrene (monomer), 1 wt % to monomer of surfactant (sodium alpha ($C_{14}$–$C_{16}$) olefin sulfonate—sold by Rhodia as Rhodacal A-246/L), and four different amounts of initiator—0.0005, 0.001, 0.002, 0.003 mole equivalents to monomer. The initiator used was an adduct of the initiator/control agent, the organic soluble 2,2,5-trimethyl-3-(1-phenylethoxy)-4-phenyl-3-azahexane. This compound predetermines the control agent to initiator ratio to equal one. Seven identical reactions were run at each initiator to monomer ratio.

A first homopolymer block was assembled in two stages, with all the components except monomer being added in the first step. In the first step, 2.5 or 1.25 wt % of styrene (25% of the total first monomer) was added to each reaction vessel, and the plate was sealed and heated at 90° C. for 2 hours. The reactor vessels were allowed to cool, were opened, and the remaining 7.5 or 3.75 wt % of styrene (75% of the first monomer) was added to each reaction vessel. The plate was then resealed and heated at 90° C. for an additional 30 hours. The reactor vessels were then cooled to room temperature and opened, and a small aliquot was taken from each vessel for analysis.

Subsequently, 0, 5, 10, 15, 20, 25 or 30 weight % of a second monomer, n-butylacrylate, was dispensed to each polymerization with the predetermined styrene to initiator ratio (4 different initiator concentrations, 7 different weight % of n-butylacrylate and 2 different weight % of styrene for a total of fifty six different polymerizations). The vessels were resealed and heated at 90° C. with mixing for an additional 30 hours. The emulsions were then worked up and characterized using the standard procedure outlined for polymerization experiments at the beginning of the Example section.

Figure 7:
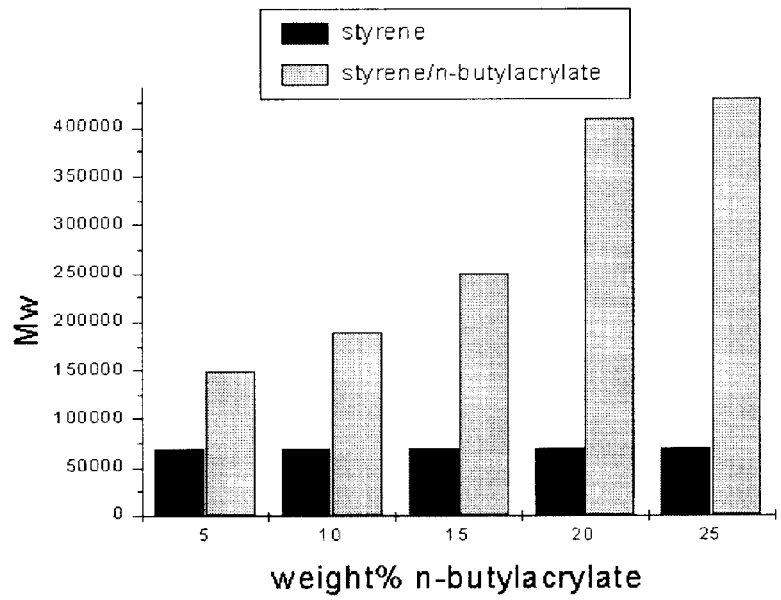
FIG. 7 is a bar graph illustrating the reinitiation of a living free radical polymerization by the addition of n-butylacrylate according to the invention.

FIG. 7 is a bar graph illustrating the reinitiation of Mw 70,000 styrene blocks with a gradient of n-butylacrylate. The final Mw of the block copolymer depends on the amount of n-butylacrylate added in the reinitiation step. Table 5 below provides selected weight average molecular weights for the styrene polymer and the block copolymer.

TABLE 5

| Wt % styrene | Wt % n-butyl-acrylate | Initiator Concentration | $M_w$ of sytrene block | $M_w$ of block copolymer |
|---|---|---|---|---|
| 10 | 5 | 0.0005 | 75,000 | 165,000 |
| 10 | 10 | 0.0005 | 75,000 | 234,000 |
| 10 | 15 | 0.0005 | 75,000 | 238,000 |
| 10 | 20 | 0.0005 | 75,000 | 248,000 |
| 10 | 25 | 0.0005 | 75,000 | 277,000 |
| 10 | 30 | 0.0005 | 75,000 | 300,000 |
| 10 | 5 | 0.001 | 48,000 | 125,000 |
| 10 | 10 | 0.001 | 48,000 | 127,000 |
| 10 | 15 | 0.001 | 48,000 | 143,000 |
| 10 | 20 | 0.001 | 48,000 | 145,000 |
| 10 | 25 | 0.001 | 48,000 | 150,000 |
| 10 | 30 | 0.001 | 48,000 | 155,000 |
| 10 | 5 | 0.002 | 20,000 | 49,000 |
| 10 | 10 | 0.002 | 20,000 | 52,000 |
| 10 | 15 | 0.002 | 20,000 | 55,000 |
| 10 | 20 | 0.002 | 20,000 | 59,000 |
| 10 | 25 | 0.002 | 20,000 | 62,000 |
| 10 | 30 | 0.002 | 20,000 | 69,000 |
| 10 | 5 | 0.003 | 17,000 | 35,000 |
| 10 | 10 | 0.003 | 17,000 | 37,000 |
| 10 | 15 | 0.003 | 17,000 | 39,000 |
| 10 | 20 | 0.003 | 17,000 | 44,000 |
| 10 | 25 | 0.003 | 17,000 | 51,000 |
| 10 | 30 | 0.003 | 17,000 | 66,000 |
| 5 | 5 | 0.0005 | 70,000 | 156,000 |
| 5 | 10 | 0.0005 | 70,000 | 183,000 |
| 5 | 15 | 0.0005 | 70,000 | 248,000 |
| 5 | 20 | 0.0005 | 70,000 | 412,000 |
| 5 | 25 | 0.0005 | 70,000 | 433,000 |
| 5 | 30 | 0.0005 | 70,000 | — |
| 5 | 5 | 0.001 | 50,000 | 100,000 |
| 5 | 10 | 0.001 | 50,000 | 105,000 |
| 5 | 15 | 0.001 | 50,000 | 110,000 |
| 5 | 20 | 0.001 | 50,000 | — |
| 5 | 25 | 0.001 | 50,000 | — |
| 5 | 30 | 0.001 | 50,000 | 197,000 |
| 5 | 5 | 0.002 | 19,000 | — |
| 5 | 10 | 0.002 | 19,000 | — |
| 5 | 15 | 0.002 | 19,000 | — |
| 5 | 20 | 0.002 | 19,000 | 61,000 |
| 5 | 25 | 0.002 | 19,000 | 98,000 |
| 5 | 30 | 0.002 | 19,000 | 102,000 |
| 5 | 5 | 0.003 | 16,000 | 41,000 |
| 5 | 10 | 0.003 | 16,000 | 45,000 |
| 5 | 15 | 0.003 | 16,000 | 46,000 |
| 5 | 20 | 0.003 | 16,000 | 50,000 |
| 5 | 25 | 0.003 | 16,000 | 52,000 |
| 5 | 30 | 0.003 | 16,000 | 59,000 |

Example 12

Forty eight stable free radical polymerization reactions were carried out under aqueous emulsion conditions. Each polymerization was set up with a total volume 0.7 mL, with 10 or 5 weight % styrene (monomer). The amount of surfactant (sodium alpha ($C_{14}$–$C_{16}$) olefin sulfonate—sold by Rhodia as Rhodacal A-246/L) added was 1 weight % to monomer, and four different amounts of initiator were added: 0.0005, 0.001, 0.002, 0.003 mole equivalents to monomer. The initiator used was an adduct of the initiator/control agent, the organic soluble 2,2,5-trimethyl-3-(1-phenylethoxy)-4-phenyl-3-azahexane. This compound predetermines the control agent to initiator ratio to equal one. Seven identical reactions were run at each initiator to monomer ratio.

A first homopolymer block was assembled in two stages, with all the components except monomer being added in the first step. In the first step, 2.5 or 1.25 wt % of styrene (25% of the total first monomer) was added to each reaction vessel, and the plate was sealed and heated at 90° C. for 2 hours. The reactor vessels were allowed to cool, were opened, and an additional 7.5 or 3.75 wt % of styrene (the remaining 75% of the first monomer) was added to each reaction vessel. The plate was then resealed and heated at 90° C. for an additional 30 hours. The reactor vessels were then cooled to room temperature and opened, and a small aliquot was taken from each vessel for analysis.

Subsequently, 0, 1, 2, 5, 7.5 or 10 weight % of a second monomer, acrylic acid, was dispensed to each polymerization with the predetermined styrene to initiator ratio (4 different initiator concentrations, 6 different weight % of acrylic acid and 2 different weight % of styrene for a total of forty eight different polymerizations). The vessels were resealed and heated at 90° C. with mixing for an additional 30 hours. The emulsions were then worked up and characterized using the standard procedure outlined for polymerization experiments at the beginning of the Example section.

Figure 8:
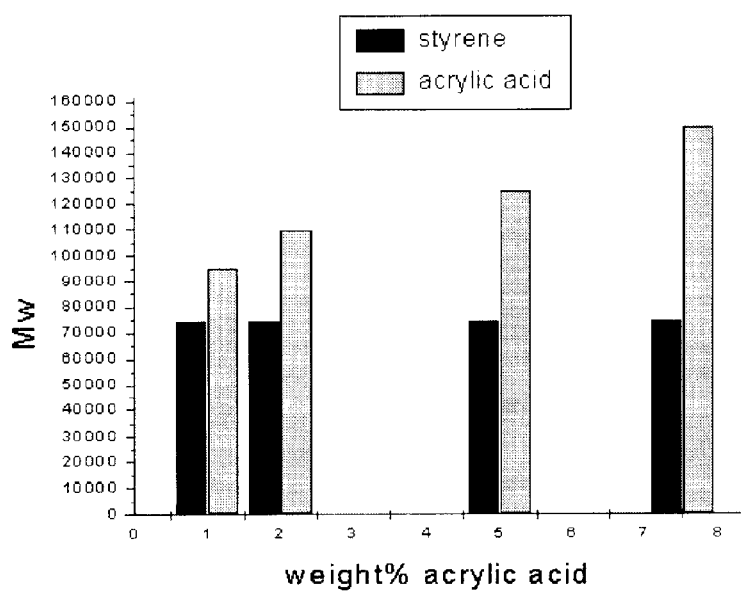
FIG. 8 is a bar graph illustrating the reinitiation of a living free radical polymerization by the addition of acrylic acid according to the invention.

FIG. 8 is a bar graph illustrating the reinitiation of Mw 75,000 styrene blocks with a gradient of acrylic acid. The final Mw of the block copolymer depends on the amount of acrylic acid added in the reinitiation step. Table 6 below provides selected weight average molecular weights for the styrene polymer and the block copolymer.

TABLE 6

| Wt % styrene | Wt % acrylic acid | Initiator Concentration | $M_w$ of sytrene block | $M_w$ of block copolymer |
|---|---|---|---|---|
| 10 | 0 | 0.0005 | 71,000 | 71,000 |
| 10 | 1 | 0.0005 | 71,000 | 95,000 |
| 10 | 2 | 0.0005 | 71,000 | 112,000 |
| 10 | 5 | 0.0005 | 71,000 | 125,000 |
| 10 | 7.5 | 0.0005 | 71,000 | 147,000 |
| 10 | 10 | 0.0005 | 71,000 | — |
| 10 | 0 | 0.001 | 51,000 | 51,000 |
| 10 | 1 | 0.001 | 51,000 | 62,000 |
| 10 | 2 | 0.001 | 51,000 | 64,000 |
| 10 | 5 | 0.001 | 51,000 | 83,000 |
| 10 | 7.5 | 0.001 | 51,000 | — |
| 10 | 10 | 0.001 | 51,000 | — |
| 10 | 0 | 0.002 | 25,000 | 25,000 |
| 10 | 1 | 0.002 | 25,000 | 27,000 |
| 10 | 2 | 0.002 | 25,000 | 28,000 |
| 10 | 5 | 0.002 | 25,000 | 29,000 |
| 10 | 7.5 | 0.002 | 25,000 | 30,000 |
| 10 | 10 | 0.002 | 25,000 | 32,000 |
| 10 | 0 | 0.003 | 19,000 | 19,000 |
| 10 | 1 | 0.003 | 19,000 | 20,000 |
| 10 | 2 | 0.003 | 19,000 | 20,000 |
| 10 | 5 | 0.003 | 19,000 | 21,000 |
| 10 | 7.5 | 0.003 | 19,000 | — |
| 10 | 10 | 0.003 | 19,000 | 25,000 |
| 5 | 0 | 0.0005 | 78,000 | 78,000 |
| 5 | 1 | 0.0005 | 78,000 | 86,000 |
| 5 | 2 | 0.0005 | 78,000 | — |
| 5 | 5 | 0.0005 | 78,000 | — |
| 5 | 7.5 | 0.0005 | 78,000 | 138,000 |
| 5 | 10 | 0.0005 | 78,000 | — |
| 5 | 0 | 0.001 | 37,000 | 37,000 |
| 5 | 1 | 0.001 | 37,000 | 42,000 |
| 5 | 2 | 0.001 | 37,000 | — |
| 5 | 5 | 0.001 | 37,000 | |

TABLE 6-continued

| Wt % styrene | Wt % acrylic acid | Initiator Concentration | $M_w$ of sytrene block | $M_w$ of block copolymer |
|---|---|---|---|---|
| 5 | 7.5 | 0.001 | 37,000 | 49,000 |
| 5 | 10 | 0.001 | 37,000 | — |
| 5 | 0 | 0.002 | 25,000 | 25,000 |
| 5 | 1 | 0.002 | 25,000 | — |
| 5 | 2 | 0.002 | 25,000 | 29,000 |
| 5 | 5 | 0.002 | 25,000 | — |
| 5 | 7.5 | 0.002 | 25,000 | 49,000 |
| 5 | 10 | 0.002 | 25,000 | — |
| 5 | 0 | 0.003 | 15,000 | 15,000 |
| 5 | 1 | 0.003 | 15,000 | — |
| 5 | 2 | 0.003 | 15,000 | 20,000 |
| 5 | 5 | 0.003 | 15,000 | — |
| 5 | 7.5 | 0.003 | 15,000 | 34,000 |
| 5 | 10 | 0.003 | 15,000 | — |

Example 13
Styrene-random-acrylic acid-block-n-butylacrylate

Ten stable free radical polymerization reactions were carried out under aqueous emulsion conditions. Each polymerization was set up to have the following final conditions for the growth of a first polymer block: a total volume 0.7 mL, with 5 weight % styrene and 1 weight % to monomer of surfactant (sodium alpha ($C_{14}$–$C_{16}$) olefin sulfonate—sold by Rhodia as Rhodacal A-246/L) and 0.003 mole equivalents of initiator to monomer. The initiator used was an adduct of the initiator/control agent, the organic soluble 2,2,5-trimethyl-3-(1-phenylethoxy)-4-phenyl-3-azahexane. This compound predetermines the control agent to initiator ratio to equal one.

A random block copolymer of styrene and acrylic acid was assembled in two stages. In the first step, 2.5 wt % of styrene (50% of the total first monomer) was added to each reaction vessel, and the plate was sealed and heated at 90° C. for 2 hours. The reactor vessels were allowed to cool, opened and an additional 2.5 wt % of styrene (the remaining 50% of the first monomer) was added to each reaction vessel. In addition, 0, 1, 2, 5 or 7.5 weight % of acrylic acid was added to each reaction vessel. The vessels were then resealed and heated at 90° C. for an additional 30 hours. After the predetermined heating and agitation time the reactor vessels were cooled to room temperature and opened and a small aliquot was taken from each vessel for analysis.

Subsequently, 5 weight % of a third monomer, n-butylacrylate, was dispensed into each vessel. The vessels were then resealed and heated to 90° C. and mixed for an additional 30 hours. The emulsions were worked up and characterized using the standard procedure outlined for polymerization experiments at the beginning of the Example section.

Figure 9:
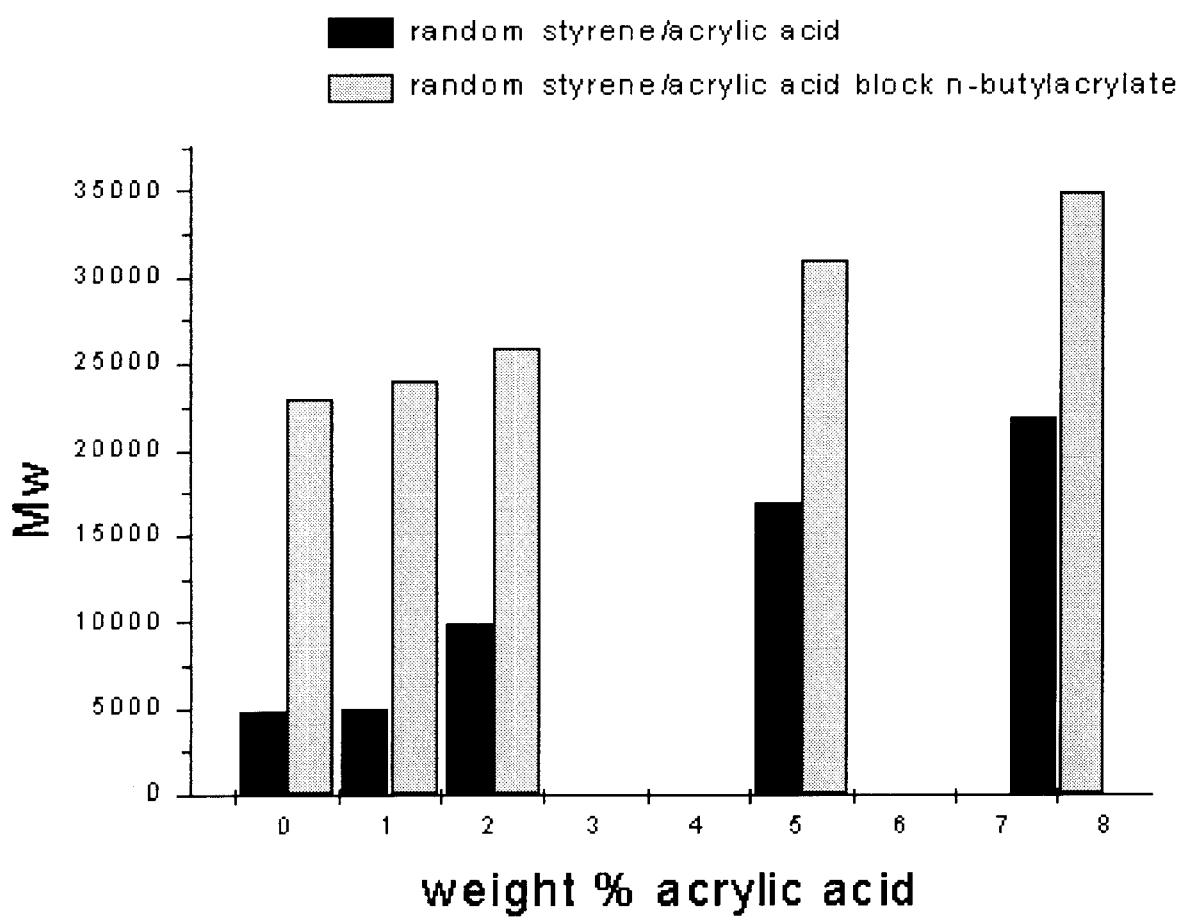
FIG. 9 is a bar graph illustrating the relationship between the overall molecular weight of the random copolymer and the amount of acrylic acid for a styrene-random-acrylic acid-block-n-butylacrylate copolymer synthesized according to the invention.

FIG. 9 is a bar graph illustrating the relationship between the overall molecular weight of the random copolymer and the amount of acrylic acid added to the emulsion polymerization. The reinitiation of this polymer with n-butylacrylate leads to a molecular weight increase as shown in Table 7.

TABLE 7

| Initiator Concentration | Wt % acrylic acid | $M_w$ of sytrene/ acrylic acid | $M_w$ of block copolymer |
|---|---|---|---|
| 0.003 | 0 | 4800 | 23,000 |
| 0.003 | 1 | 5000 | 24,000 |
| 0.003 | 2 | 10,000 | 26,000 |

TABLE 7-continued

| Initiator Concentration | Wt % acrylic acid | $M_w$ of sytrene/ acrylic acid | $M_w$ of block copolymer |
|---|---|---|---|
| 0.003 | 5 | 17,000 | 31,000 |
| 0.003 | 7.5 | 22,000 | 35,000 |

Example 14
Cyclic Nitroxide Adducts

Four stable free radical polymerization reactions were carried out under aqueous emulsion conditions. Each polymerization was set up to have the following final conditions for the growth of a first polymer block: total volume 0.7 mL, with 10 weight % of styrene (monomer). The amount of surfactant (sodium alpha ($C_{14}$–$C_{16}$) olefin sulfonate—sold by Rhodia as Rhodacal A-246/L) added was 1 weight % to monomer, and two different amounts of initiator were added: 0.001 or 0.002 mole equivalents to monomer. The initiator used was an adduct of the initiator/control agent (5.5-dimethyl-(1-pyrroline-N-oxide/AIBN adduct). This compound predetermines the control agent to initiator ratio to equal one. Four identical reactions were run at each initiator to monomer ratio.

A first homopolymer block was assembled in two stages, with all the components except monomer being added in the first step. In the first step 2.5 wt % of styrene (25% of the total first monomer) was added to each reaction vessel, and the plate was sealed and heated at 90° C. for 2 hours. The reactor vessels were allowed to cool, opened and the remaining 7.5 wt % of styrene (75% of the first monomer) was added to each reaction vessel. The plate was resealed and heated at 90° C. for an additional 30 hours. After the predetermined heating and agitation time the reactor vessels were cooled to room temperature and opened and a small aliquot was taken from each vessel for analysis.

Subsequently, 10 wt % of a second monomer, n-butylacrylate, was dispensed to half of the vessels. The vessels were then resealed and heated at 90° C. and mixed for an additional 30 hours. The emulsions were worked up and characterized using the standard procedure outlined for polymerization experiments at the beginning of the Example section. The results are set out in Table 8.

TABLE 8

| Initiator Concentration | $M_w$ of sytrene | $M_w$ of block copolymer |
|---|---|---|
| 0.001 | 98,000 | 217,000 |
| 0.002 | 24,000 | 112,000 |

Example 15
Nitroxide Adducts Containing Heterocycles

Four stable free radical polymerization reactions were carried out under aqueous emulsion conditions. Each polymerization was set up to have the following final conditions for the growth of a first polymer block: total volume of 0.7 mL, with 10 weight % of styrene (monomer), one weight % to monomer of surfactant (sodium alpha (C14C16) olefin sulfonate—sold by Rhodia as Rhodacal A-246/L), and two different amounts of initiator were added: 0.001, 0.002 mole equivalents to monomer. The initiator used was an adduct of the initiator/control agent (2,2,5-trimethyl-3-(1-pyridinylethoxy)-4-phenyl-3-azahexane. This compound predetermines the control agent to initiator ratio to equal one. Four identical reactions were run at each initiator to monomer ratio.

A first homopolymer block was assembled in two stages, with all the components except monomer being added in the first step. In the first step 2.5 wt % of styrene (25% of the total first monomer) was added to each reaction vessel, and the plate was sealed and heated at 90° C. for 2 hours. The reactor vessels were allowed to cool, were opened and the remaining 7.5 wt % of styrene (75% of the total first monomer) was added to each reaction vessel. The vessels were resealed and heated at 90° C. for an additional 30 hours. The reactor vessels were cooled to room temperature and opened and a small aliquot was taken from each vessel for analysis.

Subsequently, 10 wt % of a second monomer, n-butylacrylate, was dispensed to half of the vessels. The vessels were then resealed and heated at 90° C. and mixed for an additional 30 hours. The emulsions were worked up and characterized using the standard procedure outlined for polymerization experiments at the beginning of the Example section. The results are set out in Table 9.

TABLE 9

| Initiator Concentration | $M_w$ of sytrene | $M_w$ of block copolymer |
|---|---|---|
| 0.001 | 88,000 | 167,000 |
| 0.002 | 26,000 | 67,000 |

Example 16
Polymer Characterization
A. Particle Size Determination

Figure 10:
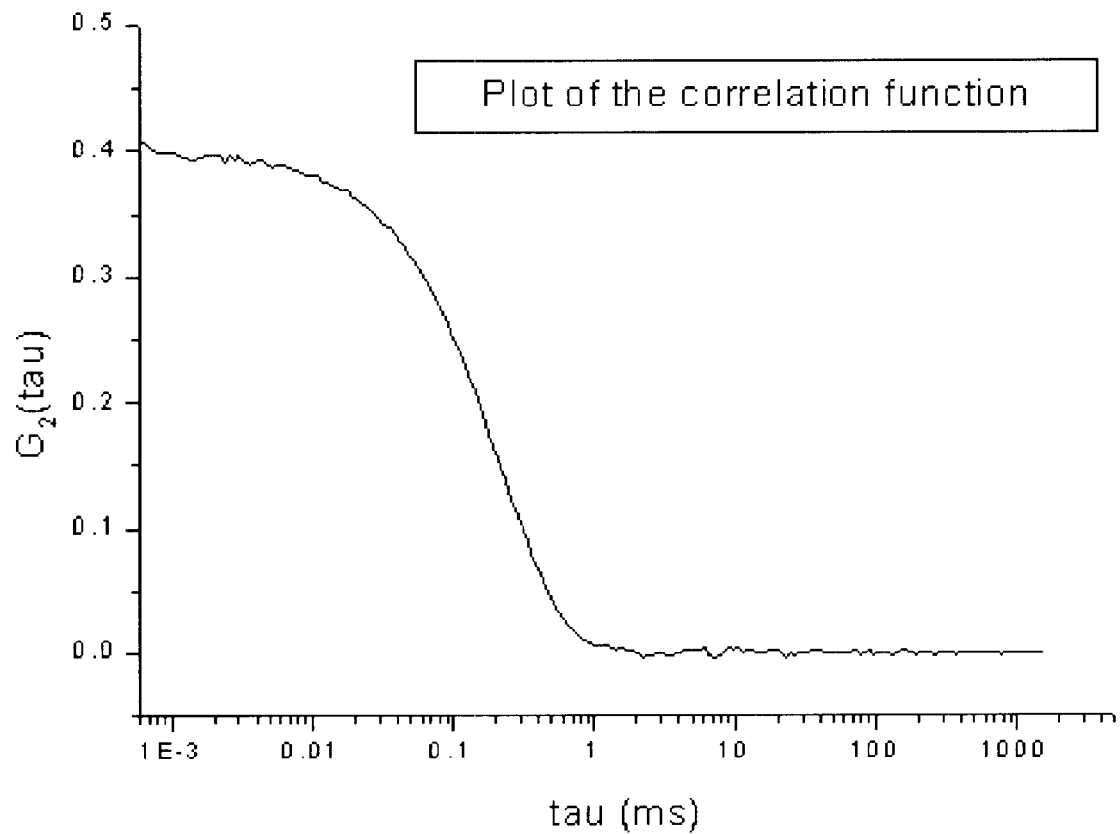
FIG. 10 illustrates a plot of an intensity-intensity autocorrelation function derived from dynamic light scattering measurements of a polymer emulsion prepared according to the invention.

Particle sizes were determined using dynamic light scattering measurements performed at a temperature of 308K in nanopure $H_2O$ on diluted latex samples, at a scattering angle of 90 degrees and a laser wavelength of 800 nm (Precision Detectors). The intensity-intensity autocorrelation function was analyzed using a second order cumulant analysis. A sample plot is illustrated in FIG. 10. In this example, the average hydrodynamic radius was 29 nm (first order cumulant) and the polydispersity index was smaller than 0.09 (second order cumulant), indicating an essentially monodisperse latex.

B. Small Angle X-Ray Scattering

Small angle X-ray scattering (SAXS) measurements were conducted using a custom laboratory source consisting of a rotating anode X-ray generator with a copper target equipped with a nickel foil filter and dual Franks mirrors for monochromatization and focussing of the beam. Films were mounted in copper blocks inside an evacuated sample chamber and annealed at 120° C. for five minutes prior to measurement at that temperature. Scattering images were recorded over 300 s by a two-dimensional multiwire area detector and reduced to a one-dimensional profile by integrating azimuthally along an arc located ±30° C. from the direction normal to the sections composing the specimen. Data were reported in the form of total counts as a function of q, the scattering momentum transfer, defined as $4\pi/\lambda \sin\theta$, where $\lambda=1.54$ Å is the wavelength of the radiation and $\theta$ is the angle between the transmitted and the scattered radiation.

Films for scattering measurements were prepared by dissolution of sufficient polymer in toluene to yield an approximate concentration of 5 wt %. The resulting solution was placed on top of a water column and the solvent was permitted to evaporate at room temperature and atmospheric pressure over 48 hours. Use of water as a casting substrate minimizes the mechanical deformation of the film upon removal from the casting vessel. The resulting polymer film was removed from the water column and dried first in air for at least 2 hours, and then in vacuum at room temperature for at least 2 hours. The film was cut into sections approximately 3×5 mm in area, and between 3 and 5 sections were stacked to yield a specimen between 1 and 2 mm in thickness. Stacked specimens were then placed in an evacuated oven and annealed for at least 48 hours at 120° C. to remove any residual solvent.

Figure 11:
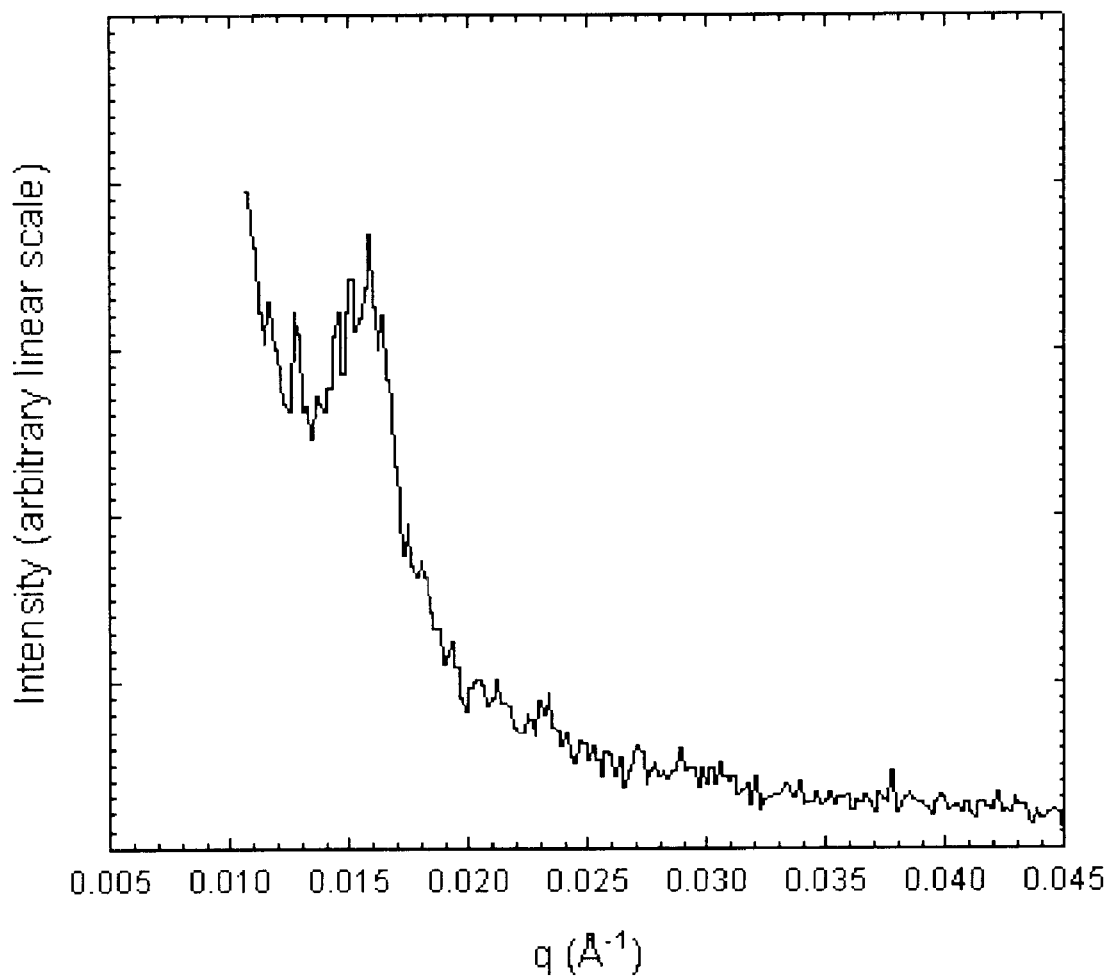
FIG. 11 illustrates the results of a small angle X-ray scattering experiment on a copolymer produced according to the invention.

FIG. 11 illustrates the results of SAXS of a polystyrene-block-poly(butyl acrylate) copolymer prepared according to Example 11, above (10 wt % styrene, 10 wt % butyl acrylate, 0.001 equivalents initiator). One scattering maximum is observed, at a position corresponding to a spatial periodicity of 417 Å. This is consistent with local phase separation of the polystyrene and poly(butyl acrylate) chains into spatially separated domains as would be expected for a block copolymer of these two monomers. A random copolymer of styrene and butyl acrylate would be compositionally homogeneous on this length scale and would not produce such a scattering maximum. A blend of polystyrene and poly(butyl acrylate) homopolymer might produce such a maximum during the early stages of macroscopic phase separation of the two polymer species, but such a peak would shift to lower values of q and approach q=0 as phase separation progressed. The persistence of this peak at a nonzero value of q after at least two days of annealing at elevated temperatures argues against this possibility.

C. Reflection Optical Microscopy

Polymer films were imaged by reflection optical micrography using a Leitz Ergolux optical microscope, operating in reflection mode at a magnification of 100×, and the images were captured with a Pixera PVC100C digital camera which was attached to the microscope. Films were prepared by dissolving the polymer in THF at a concentration of approximately 1% by weight. A small drop of the solution was deposited on a clean silicon wafer and the solvent was allowed to dry. The substrate was then annealed in a vacuum oven at 130° C. for approximately 18 hours. FIG. 12 is a sample a reflection optical micrograph from a styrene-butyl acrylate copolymer synthesized in emulsion prepared according to Example 11, above (10 wt % styrene, 10 wt % butyl acrylate, 0.001 equivalents initiator). The sharply defined, discrete interference colors are clearly visible in the image, indicating microphase separation in the copolymer. The colors vary continuously instead of discretely. The discrete colors observed in FIG. 12 constitute compelling evidence for block copolymer formation and microphase separation.

D. Transmission Electron Microscopy

Imaging of polymer films by transmission electron microscopy was performed under bright-field, in a JEOL 1200EX transmission electron microscope (TEM), with an accelerating voltage of 100 kV. Images were recorded on Kodak SO-163 film and developed according to standard procedures. Polymer films were prepared for imaging by dissolving the polymer emulsion in THF to a concentration of approximately 1% by weight. Approximately 10 μl of this solution was placed on the surface of a 200-mesh copper electron microscope grid, which was pre-coated with a thin carbon film by the supplier (SPI Supplies, part # 3520C). The carbon film, approximately 20 nm thick, spanned the holes in the copper grid and created a free-standing support for the polymer samples. The solvent was allowed to evaporate, leaving a film of the polymer on the carbon support. (Several specimens were prepared in identical manner, to allow for different staining procedures). The specimens were then annealed in a vacuum oven for approximately 18 hours at 125° C. In order to provide contrast between the domains in the electron microscope, the samples were stained with $RuO_4$ vapors ($RuO_4$ staining kit from SPI Supplies, part # 02592-AB ). An aqueous $RuO_4$ solution was prepared following the supplier's instructions. The specimen grids and an open vial containing the $RuO_4$ solution were placed underneath an inverted crystallizing dish, so that the specimens would be exposed to an atmosphere saturated with $RuO_4$ vapors. Individual specimens were removed at times of 5, 15, 30, and 60 minutes, in order to optimize the exposure time for maximum contrast. It was found that exposure times of 30 and 60 minutes gave the best results.

FIGS. 13A and 13B are reproduced from a negative which was captured at a magnification of 30,000 from a styrene-butyl acrylate polymer film prepared according to Example 11, above (10 wt % styrene, 10 wt % butyl acrylate, 0.001 equivalents initiator). The images show a region at the boundary between two sections of film having different thickness. The film thickness is restricted to a set of discrete values, as discussed above. At the boundary between these sections, a fairly regular microstructure is clearly observed. The period of the microstructure is obtained by dividing the period on the negative by the magnification, which gives approximately 1.1 mm/30,000=36 nm. The type of morphology shown in FIGS. 13A and 13B is essentially identical to that reported in B. L. Carvalho and E. L Thomas, *Phys. Rev. Lett.*, 73, pp 3321–4, for a styrene-block-isoprene copolymer with a lamellar morphology and a molecular weight of 108,000 gm/mol, using a similar sample preparation method. In both cases, the lamellae in most parts of the film lie parallel to the carbon film in most parts of the image, and are thus not visible. However the lamellae are oriented vertically at the boundaries between regions containing different number of layers, as this configuration has a lower free energy than other types of defects which could occur at such a boundary.

It is to be understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled. The disclosures of all articles, patents and references, including patent applications and publications, are incorporated herein by reference for all purposes.

What is claimed is:

1. A heterogeneous free radical polymerization process comprising:

(a) forming a heterogeneous mixture comprising water, a first amount of a first polymerizable monomer, an initiator capable of generating an initiating radical, and a control agent, the initiator and the first polymerizable monomer being present in the mixture in a ratio that is in the range of from about 1:10 to about 1:1000, the control agent being characterized by the general formula:

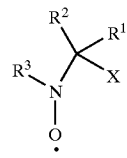

wherein X is a moiety that is capable of destabilizing the control agent on a polymerization time scale; and each $R^1$, $R^2$ and $R^3$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, and seleno;

(b) heating the mixture at a temperatures of about 100° C. or less for a time sufficient to form a polymer, such that substantially no unreacted initiator remains in the mixture; and (c) adding a second amount of the first polymerizable monomer to the mixture and heating the mixture to continue propagation of the polymer.

2. The method of claim 1, wherein X is hydrogen.

3. The method of claim 1, wherein $R^1$ and $R^2$ are joined together in a ring structure.

4. The method of claim 1, wherein $R^2$ and $R^3$ are joined together in a ring structure.

5. The method of claim 1, wherein $R^1$ is selected from the group consisting of alkyl, substituted alkyl, cycloalkyl, substituted cycloalkyl, aryl, and substituted aryl.

6. The method of claim 5, wherein $R^1$ is phenyl.

7. The method of claim 5, wherein $R^1$ is pyridyl.

8. The method of claim 1, wherein $R^2$ is selected from the group consisting of alkyl and substituted alkyl.

9. The method of claim 8, wherein $R^2$ is isopropyl.

10. The method of claim 1, wherein $R^3$ is selected from the group consisting of alkyl, substituted alkyl and heteroalkyl.

11. The method of claim 10, wherein $R^3$ is either tert-butyl or $Me_3SiOCH_2(CH_3)_2C-$.

12. The method of claim 1, wherein the control agent is a nitroxide having the formula:

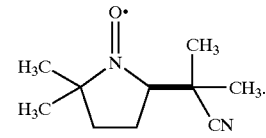

13. The method of claim 1, wherein the initiator is selected from the group consisting of water soluble free radical initiators and solvent soluble free radical initiators.

14. The method of claim 13, wherein the initiator is selected from the group consisting of peroxides, persulfates and azo compounds.

15. The method of claim 1, wherein the mixture comprises a surfactant.

16. The method of claim 15, wherein the surfactant is selected from the group consisting of ionic and non-ionic surfactants.

17. The method of claim 1, wherein the first polymerizable monomer is a vinyl monomer.

18. The method of claim 17 wherein the first polymerizable monomer is a vinyl monomer selected from the group consisting of styrene, substituted styrene, alkyl acrylate, substituted alkyl acrylate, alkyl methacrylate, substituted alkyl methacrylate, acrylic acid, methacrylic acid, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, and vinyl acetate.

19. The method of claim 1, wherein the mixture comprises an accelerator.

20. The method of claim 1, wherein the ratio of control agent to initiating radical is in the range of from about 0.1:1 to about 2:1 equivalents.

21. The method of claim 1, wherein the heterogeneous mixture is a traditional emulsion.

22. The method of claim 1, wherein the heterogeneous mixture is a mini emulsion.

23. The method of claim 1, wherein the heterogeneous mixture is a micro emulsion.

24. The method of claim 1, wherein the heterogeneous mixture is a suspension.

25. The method of claim 1, wherein the heterogeneous mixture is a dispersion.

26. The process of claim 1, further comprising:
(d) sequentially adding a second polymerizable monomer to the mixture after adding the second amount of the first polymerizable monomer to form a copolymer of the first and second polymerizable monomers.

27. The method of claim 26, wherein the copolymer comprises a block copolymer having a plurality of blocks.

28. The method of claim 26, wherein the copolymer comprises a random copolymer or higher order interpolymer.

29. The method of claim 1, wherein the weight average molecular weight of the polymer is greater than about 25,000.

30. The method of claim 1, wherein the weight average molecular weight of the polymer is greater than about 50,000.

31. The method of claim 1, wherein the weight average molecular weight of the polymer is greater than about 75,000.

32. The method of claim 1, wherein the weight average molecular weight of the polymer is greater than about 100,000.

33. The method of claim 27, wherein the weight average molecular weight of a block of the block copolymer is greater than about 25,000.

34. The method of claim 27, wherein the weight average molecular weight of a block of the block copolymer is greater than about 50,000.

35. The method of claim 27, wherein the weight average molecular weight of a block of the block copolymer is greater than about 100,000.

36. The method of claim 27, wherein the weight-average molecular weight of each of a plurality of blocks of the block copolymer is greater than about 25,000.

37. The method of claim 27, wherein the weight average molecular weight of each of a plurality of blocks of the block copolymer is greater than about 100,000.

38. The method of claim 1, further comprising controlling the weight average molecular weight of the polymer.

39. The method of claim 1, further comprising controlling the average particle diameter of the polymer.

40. The method of claim 1, wherein: the mixture includes a plurality of particles having an average particle diameter in the range from about 20 nanometers to about 300 nanometers.

41. The method of claim 1, further comprising re-initiating the propagation of the polymer by the addition after step (c) of a reinitiation monomer, the reinitiation monomer being selected from the group consisting of the first polymerizable monomer and a second polymerizable monomer.

42. The method of claim 1, wherein forming a mixture of water, a first polymerizable monomer, an initiator and a control agent comprises generating the control agent in situ from a nitrone.

43. The method of claim 1, wherein forming a mixture of water, a first polymerizable monomer, an initiator and a control agent comprises mixing water, the first polymerizable monomer, a free radical initiator and a nitroxide control agent.

44. The method of claim 1, wherein forming a mixture of water, a first polymerizable monomer, an initiator and a control agent comprises mixing water, the first polymerizable monomer and a control agent-initiator adduct, wherein the control agent-initiator adduct is characterized by the general formula:

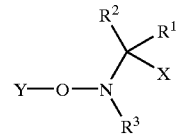

wherein Y is a residue capable of initiating a free radical polymerization upon homolytic cleavage of the Y—O bond, the residue being selected from the group consisting of fragments derived from a free radical initiator, alkyl, substituted alkyl, alkoxy, substituted alkoxy, aryl, and substituted aryl.

45. The method of claim 44, wherein Y is 1-phenylethyl.

46. The method of claim 44, wherein Y is 1-(4-pyridyl)ethyl.

47. The method of claim 44, wherein the adduct has the formula:

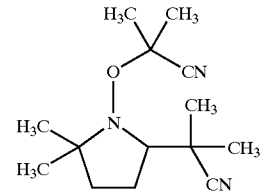

48. The method of claim 44, wherein Y forms a water-soluble free radical upon homolytic cleavage of the Y—O bond.

49. The method of claim 1, wherein the polymer after step (c) has a polydispersity of less than about 2.0.

50. The method of claim 1, wherein the polymer after step (c) has a polydispersity of less than about 1.5.

51. The method of claim 1, wherein the polymer after step (c) has a polydispersity of less than about 1.3.

52. The process of claim 1, wherein the conversion of the first polymerizable monomer in step (c) is at least 70%.

53. The process of claim 1, further comprising:
(e) neutralizing the control agent when the conversion of the first polymerizable monomer in step (c) reaches greater than about 80%.

54. The process of claim 1, wherein heating the mixture at a temperature of about 100° C. or less for a time sufficient to form a polymer comprises forming a plurality of polymer chains, greater than 80 percent of the chains having living free radical polymerization kinetics.

55. The method of claim 1, wherein:

the mixture has a solids content of greater than or equal to about 40%.

56. The method of claim 15, wherein:

the surfactant is present in a quantity in the range from about 0.1 to about 5% by weight relative to the first polymerizable monomer.

57. The method of claim 15, wherein:

the surfactant is present in a quantity in the range from about 0.1 to about 2% by weight relative to first polymerizable monomer.

58. The method of claim 40, wherein:

the plurality of particles have an average particle diameter in the range from about 40 nanometers to about 140 nanometers.

59. The method of claim 1, wherein:

the polymer is formed with a conversion of the first polymerizable monomer of greater than about 70% by weight.

60. The method of claim 1, wherein:

the polymer is formed with a conversion of the first polymerizable monomer of greater than about 90% by weight.

* * * * *